(12) United States Patent
Tipler et al.

(10) Patent No.: US 8,561,484 B2
(45) Date of Patent: Oct. 22, 2013

(54) SORBENT DEVICES WITH LONGITUDINAL DIFFUSION PATHS AND METHODS OF USING THEM

(75) Inventors: Andrew Tipler, Trumbull, CT (US); Avinash Dalmia, Hamden, CT (US)

(73) Assignee: PerkinElmer Health Sciences, Inc., Waltham, MA (US)

( * ) Notice: Subject to any disclaimer, the term of this patent is extended or adjusted under 35 U.S.C. 154(b) by 712 days.

(21) Appl. No.: 12/729,432

(22) Filed: Mar. 23, 2010

(65) Prior Publication Data

US 2010/0242579 A1 Sep. 30, 2010

Related U.S. Application Data

(60) Provisional application No. 61/162,749, filed on Mar. 24, 2009.

(51) Int. Cl.
*G01N 1/22* (2006.01)
*G01N 1/40* (2006.01)
*G01N 25/00* (2006.01)
*G01N 30/54* (2006.01)
*G01N 30/60* (2006.01)

(52) U.S. Cl.
USPC ....... 73/863.21; 73/23.39; 73/23.4; 73/23.41; 73/25.01; 73/31.07; 73/863.12; 73/863.23; 422/430

(58) Field of Classification Search
USPC .............. 73/1.03, 23.39–23.41, 25.01, 25.05, 73/31.07, 863.12–863.21, 863.23, 863.31, 73/864.73, 864.81, 864.85; 422/88–89, 422/430, FOR. 106
See application file for complete search history.

(56) References Cited

U.S. PATENT DOCUMENTS

| | | | | |
|---|---|---|---|---|
| 2,211,162 | A | * | 8/1940 | Logan et al. ................ 95/11 |
| 2,339,651 | A | * | 1/1944 | Rearden et al. .............. 422/88 |
| 2,398,817 | A | * | 4/1946 | Turner ........................ 95/87 |
| 3,070,532 | A | * | 12/1962 | Zebroski .................... 376/253 |
| 3,537,237 | A | * | 11/1970 | Gardner ...................... 95/23 |
| 3,545,929 | A | * | 12/1970 | Swinnerton et al. ...... 422/89 X |
| 3,791,106 | A | * | 2/1974 | Haley ........................ 96/10 |
| 3,834,122 | A | * | 9/1974 | Allison et al. .............. 95/122 |

(Continued)

FOREIGN PATENT DOCUMENTS

EP 820972 A1 * 1/1998
JP 11295284 A * 10/1999

(Continued)

OTHER PUBLICATIONS

International Report on Patentability for PCT/US2009/045300 mailed Nov. 30, 2010.

(Continued)

*Primary Examiner* — Thomas P Noland
(74) *Attorney, Agent, or Firm* — Rhodes IP PLC; Christopher R Rhodes

(57) ABSTRACT

Certain aspects and examples are directed to sorbent devices and methods of using them. In certain embodiments, a sorbent device comprising a body comprising a sampling inlet, a base and a longitudinal diffusion path between the inlet and the base is provided. In some embodiments, the sorbent device can include at least two sorbent materials fluidically coupled to the longitudinal diffusion path, in which the sorbent materials are arranged from a material with a weakest sorbent strength to a material with a strongest sorbent strength with the weakest sorbent strength material adjacent to the sampling inlet.

20 Claims, 20 Drawing Sheets

(56) References Cited

U.S. PATENT DOCUMENTS

| | | | |
|---|---|---|---|
| 4,180,389 A * | 12/1979 | Paul | 95/11 |
| 5,933,357 A | 8/1999 | Tipler | |
| 5,958,246 A | 9/1999 | Tipler | |
| 6,112,602 A * | 9/2000 | Mitra | 73/863.12 |
| 6,226,852 B1 * | 5/2001 | Gundel et al. | 29/458 |
| 6,402,813 B2 | 6/2002 | Monereau | |
| 6,494,939 B1 | 12/2002 | Tipler | |
| 6,619,143 B2 * | 9/2003 | Danylewych-May et al. | 73/863.21 |
| 6,645,773 B2 | 11/2003 | Tipler | |
| 6,645,908 B1 * | 11/2003 | Sigman et al. | 502/405 |
| 6,652,625 B1 | 11/2003 | Tipler | |
| 6,814,785 B2 | 11/2004 | Tipler | |
| 6,974,495 B2 | 12/2005 | Tipler | |
| 7,013,707 B2 | 3/2006 | Prohaska | |
| 7,111,494 B2 | 9/2006 | Tipler | |
| 7,168,296 B2 | 1/2007 | Tipler | |
| 7,219,532 B2 | 5/2007 | Tipler | |
| 7,237,430 B2 | 7/2007 | Prohaska | |
| 7,267,709 B2 | 9/2007 | Tipler | |
| 7,284,410 B2 | 10/2007 | Tipler | |
| 7,311,757 B2 | 12/2007 | Tipler | |
| 7,422,625 B2 | 9/2008 | Tipler | |
| 7,459,313 B2 | 12/2008 | Tipler | |
| 7,468,095 B2 | 12/2008 | Tipler | |
| 7,534,286 B2 | 5/2009 | Tipler | |
| 7,552,618 B2 | 6/2009 | Tipler | |
| 7,572,319 B2 | 8/2009 | Tipler | |
| 7,662,630 B2 | 2/2010 | Tipler | |
| 7,691,181 B2 | 4/2010 | Tipler | |
| 7,709,267 B2 | 5/2010 | Tipler | |
| 7,824,478 B2 | 11/2010 | Tipler | |
| 8,017,081 B2 | 9/2011 | Tipler | |
| 8,388,736 B2 * | 3/2013 | Marotta et al. | 73/23.41 X |
| 2002/0134173 A1 | 9/2002 | Lindgren | |
| 2002/0157483 A1 | 10/2002 | Lo | |
| 2003/0113538 A1 | 6/2003 | Tom | |
| 2003/0156987 A1 | 8/2003 | Tipler | |
| 2003/0164312 A1 | 9/2003 | Prohaska | |
| 2004/0014232 A1 | 1/2004 | Tipler | |
| 2004/0016341 A1 | 1/2004 | Tipler | |
| 2005/0039602 A1 | 2/2005 | Tipler | |
| 2005/0180893 A1 | 8/2005 | Handly | |
| 2005/0193802 A1 | 9/2005 | Tipler | |
| 2005/0210957 A1 | 9/2005 | Tipler | |
| 2005/0284209 A1 | 12/2005 | Tipler | |
| 2006/0016245 A1 | 1/2006 | Tipler | |
| 2006/0021504 A1 | 2/2006 | Tipler | |
| 2006/0075802 A1 | 4/2006 | Prohaska | |
| 2006/0094118 A1 | 5/2006 | Tipler | |
| 2006/0099716 A1 | 5/2006 | Tipler | |
| 2006/0099718 A1 | 5/2006 | Tipler | |
| 2006/0245975 A1 | 11/2006 | Tipler | |
| 2006/0260383 A1 | 11/2006 | Tipler | |
| 2006/0263901 A1 | 11/2006 | Tipler | |
| 2006/0278076 A1 | 12/2006 | Tipler | |
| 2007/0068685 A1 | 3/2007 | Tippler | |
| 2007/0261474 A1 | 11/2007 | Tipler | |
| 2007/0295057 A1 | 12/2007 | Tipler | |
| 2008/0041137 A1 | 2/2008 | Tipler | |
| 2008/0098887 A1 | 5/2008 | Tipler | |
| 2008/0105033 A1 | 5/2008 | Tipler | |
| 2009/0000481 A1 | 1/2009 | Tipler | |
| 2009/0052497 A1 | 2/2009 | Tipler | |
| 2009/0084261 A1 | 4/2009 | Tipler | |
| 2009/0277245 A1 | 11/2009 | Tipler | |
| 2010/0101411 A1 | 4/2010 | Tipler | |
| 2010/0242579 A1 | 9/2010 | Tipler | |
| 2011/0079143 A1 | 4/2011 | Marotta | |

FOREIGN PATENT DOCUMENTS

| | | |
|---|---|---|
| RU | 2083982 C1 * | 7/1997 |
| WO | WO 9103719 A * | 3/1991 |
| WO | 00/45929 | 8/2000 |
| WO | 02/44684 | 6/2002 |
| WO | 2006024851 | 3/2006 |
| WO | WO 2007148084 A1 * | 12/2007 |

OTHER PUBLICATIONS

International Preliminary Report on Patentability for PCT/US20101028236 mailed on Sep. 27, 2011.

International Search Report for PCT/US2010/50828 mailed on Nov. 19, 2010.

Batterman. J. Environ. Monit. (2002), vol. 4, pp. 870-878, Diffusive uptake in passive and active absorbent sampling using thermal desorption tubes.

Harper. J .Chrom. A. vol. 885, pp. 129-151, Sorben trapping of volatile organic compounds from air, 2000.

ISR/WO from PCT/US2010/028236, mailed May 20, 2010.

* cited by examiner

SORBENT DEVICES WITH LONGITUDINAL DIFFUSION PATHS AND METHODS OF USING THEM

PRIORITY APPLICATION

This application claims priority to U.S. Provisional Application No. 61/162,749 filed on Mar. 24, 2009, the entire disclosure of which is hereby incorporated herein by reference for all purposes.

TECHNOLOGICAL FIELD

Certain features, aspect and embodiments are directed to sorbent devices that include a longitudinal diffusion path to permit passive sampling of species. In particular, certain embodiments are directed to multi-bed sorbent tubes that include an internal, longitudinal diffusion path to permit passive sampling of samples that include a plurality of species having varying boiling points.

BACKGROUND

One common application of chromatographic analysis is the use of thermal desorption units to determine the constituents of a particular environment. For example, it is often desired to detect the amount of volatile organic compounds (VOCs) present in a certain sample of air. One way of doing this is by first transporting a sorbent tube packed with an adsorbent material into the environment to be tested, and allowing the VOCs in the air to be collected. In each case, the analytes to be measured (i.e., the VOCs) are retained by the adsorbent as the air passes through the tube.

SUMMARY

In one aspect, a sorbent device comprising a body comprising a sampling inlet, and a longitudinal diffusion path between the sampling inlet and the base of the device is provided. In some examples, the sorbent device can include at least one sorbent material fluidically coupled to the longitudinal diffusion path. In other examples, the sorbent device can include a serial arrangement of at least two different sorbent materials each fluidically coupled to the longitudinal diffusion path, in which the sorbent materials are arranged from a material with a weakest sorbent strength to a material with a strongest sorbent strength with the weakest sorbent strength material adjacent to the sampling inlet. In some embodiments, the sorbent device is effective to sample passively an air space comprising volatile species.

In certain embodiments, the device can include a fluid permeable barrier between the at least two different sorbent materials. In some embodiments, the sorbent device can include at least four different sorbent materials, in which the sorbent materials are arranged from a material with a weakest sorbent strength to a material with a strongest sorbent strength with the weakest sorbent strength material adjacent to the sampling inlet. In other embodiments, the sorbent device can include at least six different sorbent materials, in which the sorbent materials are arranged from a material with a weakest sorbent strength to a material with a strongest sorbent strength with the weakest sorbent strength material adjacent to the sampling inlet. In certain embodiments, the sorbent device can include an air gap between the sampling inlet and the weakest strength sorbent material. In additional embodiments, the surface area of the sorbent material having the strongest sorbent strength is greater than the surface area of the sorbent material having the weakest sorbent strength. In some examples, the sorbent device can include a carrier in longitudinal diffusion path of the sorbent device. In other examples, the sorbent material or materials can be disposed in the carrier. In some examples, the sorbent material or materials can be disposed between the carrier and an inner surface of the sorbent device. In certain examples, the sorbent device can include a void space between the at least two different sorbent materials. In additional examples, the longitudinal diffusion path can include a variable cross-sectional diameter. In certain embodiments, the longitudinal diffusion path can include an opening that spans the full length of the longitudinal diffusion path from the sampling inlet to the sampling outlet. In some embodiments, the base can be configured to couple to an additional sorbent device comprising a longitudinal diffusion path. In other embodiments, at least one of the sampling outlet and the base comprises a coupling configured to couple to the additional sorbent device, in which coupling of the sorbent device to the additional sorbent device provides fluidic coupling between the longitudinal diffusion path of the sorbent device and the longitudinal diffusion path of the additional sorbent device. In further embodiments, the sorbent device can include a cover coupled to the device base, the cover configured to prevent entry of sample into the sorbent device through the base. In additional embodiments, the device can include a cover coupled to the sampling inlet, the cover configured to permit flow of air into the sorbent device in an open position and prevent flow of air into the sorbent device in a closed position.

In an additional aspect, a sorbent device comprising a hollow tube comprising a sampling inlet and a base or sampling outlet, the hollow tube comprising an interior volume in which at least two different sorbent materials are disposed, the interior volume comprising a longitudinal diffusion path between the sampling inlet and the base is disclosed. In some examples, the longitudinal diffusion path is fluidically coupled to at least one sorbent material or at least two sorbent materials, in which the sorbent materials are arranged serially from a material with a weakest sorbent strength to a material with a strongest sorbent strength with the weakest sorbent strength material adjacent to the sampling inlet. In certain examples, the sorbent device is effective to sample passively an air space comprising volatile species.

In certain embodiments, the at least two different sorbent materials are separated from each other by a fluid permeable barrier. In other embodiments, the sorbent device can include a void space between the at least two different sorbent materials. In further embodiments, the sorbent device can include at least four different sorbent materials disposed in the body, in which the sorbent materials are arranged from a material with a weakest sorbent strength to a material with a strongest sorbent strength with the weakest sorbent strength material adjacent to the sampling inlet. In some examples, the sorbent device can include a carrier in the interior volume. In other examples, the sorbent material or materials can be disposed in the carrier. In additional examples, the sorbent material or materials can be disposed between the carrier and an inner surface of the sorbent device. In some embodiments, the hollow tube comprises stainless steel, and the four sorbent materials are independently selected from the group consisting of a charcoal, a carbon black, a carbon-molecular sieve, a porous polymer, a silicone, a molecular sieve, and a silica gel. In other embodiments, the sorbent device can include at least six different sorbent materials, in which the sorbent materials are arranged from a material with a weakest sorbent strength to a material with a strongest sorbent strength with the weakest sorbent strength material adjacent to the sampling inlet. In some embodiments, the device further includes an air gap between the sampling inlet and the weakest strength sorbent material. In further embodiments, the surface area of the sorbent material having the strongest sorbent strength is greater than the surface area of the sorbent material having the weakest sorbent strength. In some examples, the longitudinal diffusion path can include a variable cross-sectional diameter. In additional examples, the longitudinal diffusion path comprises an opening that spans the full length of the longitudinal diffusion path from the sampling inlet to the sampling outlet. In certain examples, the longitudinal diffusion path comprises a non-uniform cross-sectional shape. In further examples, at least one of the base and the sampling inlet comprises a coupling configured to couple to an additional sorbent device comprising a longitudinal diffusion path, in which coupling of the sorbent device to the additional sorbent device provides fluidic coupling between the longitudinal diffusion path of the sorbent device and the longitudinal diffusion path of the additional sorbent device. In some examples, the sorbent device can include a cover coupled to the base, the cover configured to prevent entry of sample into the sorbent device through the sampling outlet.

In another aspect, a kit comprising a sorbent device comprising a body comprising a sampling inlet, a base, and a longitudinal diffusion path between the sampling inlet and the base, the sorbent device further comprising a serial arrangement of at least two different sorbent materials each fluidically coupled to the longitudinal diffusion path, in which the sorbent materials are arranged from a material with a weakest sorbent strength to a material with a strongest sorbent strength with the weakest sorbent strength material adjacent to the sampling inlet, in which the sorbent device is effective to sample passively an air space comprising volatile species is provided.

In certain examples, the kit can include an additional sorbent device configured to passively sample air in an environment, the additional sorbent device comprising a body comprising a sampling inlet, a base and a longitudinal diffusion path between the sampling inlet and the base, the additional sorbent device further comprising at least one sorbent material fluidically coupled to the longitudinal diffusion path of the additional sorbent device, in which the sorbent material of the additional sorbent device is different from the sorbent materials of the sorbent device. In further examples, the additional sorbent device can include a coupling configured to couple to the sorbent device to provide fluidic coupling between the longitudinal diffusion path of the sorbent device and the longitudinal diffusion path of the additional sorbent device. In some examples, the kit can include at least one standard. In other examples, the kit can include a cover configured to couple to the base to prevent sample from entering the sorbent device through the sampling outlet. In additional examples, the kit can include a cover configured to couple to the sampling inlet to prevent fluid from entering the sampling inlet. In certain examples, the kit can include a plurality of additional sorbent devices each comprising a body comprising a sampling inlet, a base, a longitudinal diffusion path between the sampling inlet and the base, in which the plurality of additional sorbent devices each comprise a different sorbent medium than present in the sorbent device, and in which the plurality of additional sorbent devices each comprise a coupling to provide fluidic coupling between the longitudinal diffusion paths. In other examples, the kit can include instructions for sampling the air in the environment using the sorbent device. In further examples, the kit can include a thermal desorption analyzer for use with the sorbent device. In some examples, the kit can include a coupling on the body, the coupling configured to attach the sorbent device to a structure.

In an additional aspect, a method comprising exposing a sorbent device to an environment comprising volatile species to permit volatile species in the environment to passively adsorb to the sorbent device is provided. In some examples, the method can include exposing a sorbent device that comprises a sampling inlet, a base and a longitudinal diffusion path between the sampling inlet and the base, the longitudinal diffusion path fluidically coupled to at least two different sorbent materials in the sorbent device that are arranged serially from a material with a weakest sorbent strength to a material with a strongest sorbent strength with the weakest sorbent strength material adjacent to the sampling inlet.

In certain examples, the method can include desorbing the species adsorbed to the sorbent device. In other examples, the method can include fluidically coupling the sorbent device to a thermal desorption analyzer. In additional examples, the method can include configuring the sorbent device with at least four different sorbent materials disposed serially in the cavity, in which the sorbent materials are arranged serially from a material with a weakest sorbent strength to a material with a strongest sorbent strength with the weakest sorbent strength material adjacent to the sampling inlet. In some examples, at least one of the four different sorbent materials comprises a graphitized carbon black. In other examples, each of the four different sorbent materials independently is a graphitized carbon black or a carbon molecular sieve with none of the materials being the same material. In further examples, the strongest sorbent material is disposed adjacent to the device base, the weakest sorbent material is disposed adjacent to the sampling inlet and the other sorbent materials are between the strongest sorbent material and the weakest sorbent materials and arranged in order from weakest sorbent strength to strongest sorbent strength. In other examples, the method can include configuring at least one of the sampling inlet and the base to include a coupling configured to couple to an additional sorbent device comprising a longitudinal diffusion path, in which coupling of the sorbent device to the additional sorbent device provide fluidic coupling between the longitudinal diffusion path of the sorbent device and the longitudinal diffusion path of the additional sorbent device. In additional examples, the method can include coupling the sorbent device to a thermal desorption analyzer and desorbing the adsorbed species in the sorbent device. In some examples, the method can include providing an additional sorbent device comprising a sampling inlet, a base and a longitudinal diffusion path between the sampling inlet and the base and fluidically coupled to at least one sorbent material in the additional sorbent device.

In another aspect, a method of facilitating passive sampling of an air space is provided. In certain examples, the method can include providing a sorbent device comprising a body comprising a sampling inlet, a base and a longitudinal diffusion path between the sampling inlet and the base, the sorbent device further comprising a serial arrangement of at least two different sorbent materials each fluidically coupled to the longitudinal diffusion path, in which the sorbent materials are arranged from a material with a weakest sorbent strength to a material with a strongest sorbent strength with the weakest sorbent strength material adjacent to the sampling inlet, in which the sorbent device is effective to adsorb volatile species in the air space to sample passively the air space.

In an additional aspect, a sorbent device comprising a first sampling inlet, a second sampling inlet and a longitudinal diffusion path between the sampling inlets is described. In some examples, two or more sorbent materials are present in the sorbent device and are each fluidically coupled to the longitudinal diffusion path. In certain embodiments, the sorbent materials are present in a palindromic arrangement in the sorbent device. In other examples, the sorbent device can include a gas port configured to provide a carrier gas to the sorbent device.

Additional features, aspects, examples and embodiments are described in more detail below.

BRIEF DESCRIPTION OF THE FIGURES

Certain illustrative embodiments are described in more detail below with reference to the accompanying figures in which.

Figure 1:
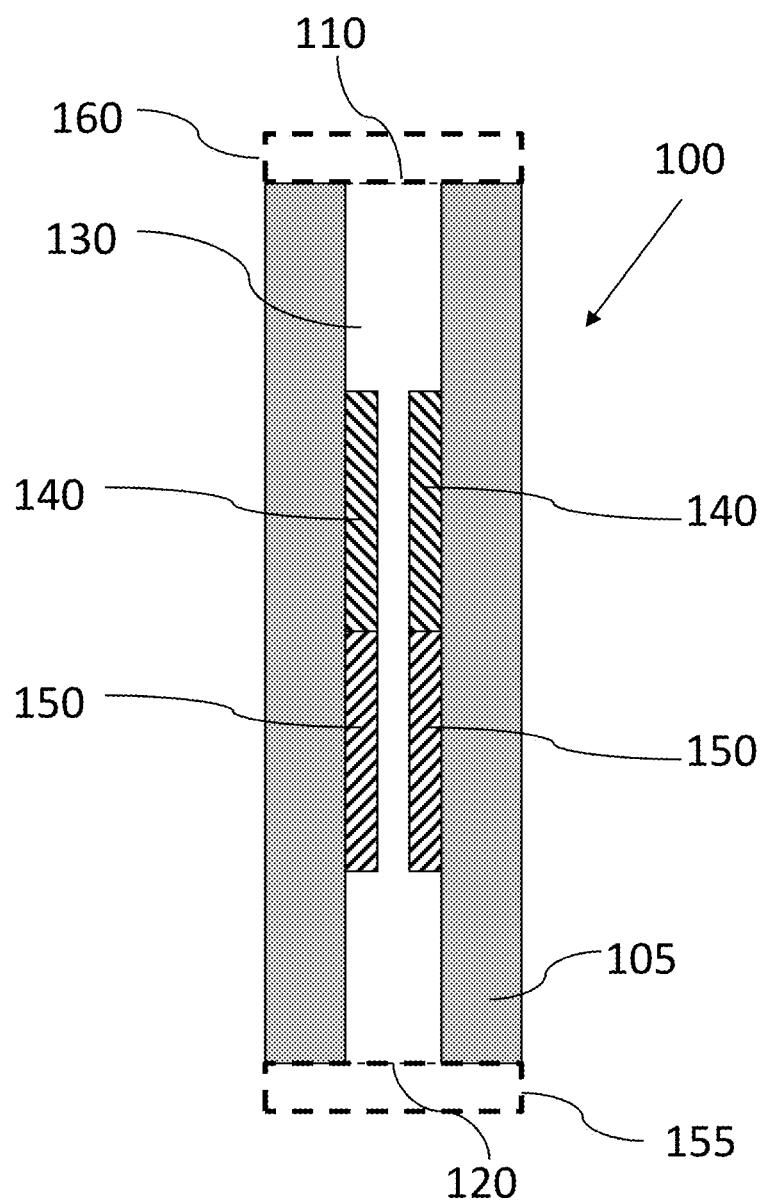
FIG. 1 is an illustration of a sorbent device including a longitudinal diffusion path, in accordance with certain examples.

Certain dimensions and components shown in the figures may have been enlarged, distorted, exaggerated or otherwise shown in a non-conventional manner to facilitate a better understanding of the technology described herein. The lengths, widths, cross-sectional shapes and the like shown in the figures are merely illustrative, and other lengths, widths and cross-sectional shapes will be readily selected by the person of ordinary skill in the art, given the benefit of this disclosure.

DETAILED DESCRIPTION

Examples of the sorbent devices described herein can be used in many different applications including, but not limited to, indoor and outdoor air monitoring, analysis of the offgasing of soil, water, biofuels, polymers, packaging materials, flavors and fragrances, cosmetics, exhaust gases, and many other applications where volatile species may be present. The particular materials selected for inclusion in the sorbent devices may vary depending on the particular species to be analyzed. The term sorbent device is used for convenience purposes only, and the sorbent devices described herein are effective to adsorb (or absorb) and desorb analyte species. In certain embodiments, by selecting combinations of different sorbent materials, the sorbent devices are effective to passively sample air species including samples having a broad molecular weight range of analytes.

In certain embodiments, the sorbent devices described herein include two or more different types of a packing material, also referred to herein as a sorbent material that can be used for adsorption. In some examples described herein, each sorbent material can be present in an individual sorbent device that is coupled or plugged to another sorbent device including a different sorbent material such that the diffusion paths of each device are fluidically coupled to each other.

In certain examples, the sorbent devices described herein can be used with chromatographic analysis to determine the constituents of a particular environment. For example, it is often desirable to detect the amount of volatile organic compounds (VOCs) present in a certain sample of air. The VOCs may be collected by drawing a sample of gas (typically ambient air) through such a tube using a syringe, small vacuum pump, or other means. This latter method is commonly referred to as "pumped sampling." In each case, the analytes to be measured, e.g., the VOCs, are retained by the sorbent material as the air passes through the sorbent device. Once the VOCs are collected, the sorbent device having the adsorbed analytes is subsequently heated in a thermal desorption instrument, and a flow of inert gas, such as helium, nitrogen or hydrogen, is provided to sweep the VOCs out of the sorbent device and into a chromatographic column for separation and analysis.

In certain examples, the sorbent devices disclosed herein can be advantageously used in passive sampling processes where ambient air is permitted to diffuse into the sorbent device without the assistance of a pump or other means. Passive sampling permits the use of fewer mechanical parts, uses substantially no energy and increases the overall applications of the sorbent devices described herein. In particular, the sorbent devices described herein can be used in any setting where it is desirable to analyze species in an air source using diffusive monitoring. Such air sources may exist, for example, in industrial settings, home settings or in other settings that may include one or more species dissolved in the ambient air (or other air sources).

In certain examples, the sorbent devices described herein can be used in soil vapor intrusion analyses. Soil vapor intrusion occurs when toxic compounds that are present in the air space in soil of a contaminated location enter a building, potentially creating a health risk. Many contaminated sites have high diesel levels and toxic polynuclear aromatic compounds, in addition to the current EPA air toxics list of components. When sampling sites using currently available desorption tubes, diesel entering the tube would not be easily released thereby rendering the tube unusable for re-sampling. In addition, because of the strong adsorptive nature of the tube, polynuclear aromatic compounds with boiling points above naphthalene are not quantitatively desorbed from the tube, making the quantitative investigation of these compounds difficult or not possible. Also, when initially sampling a site, there are many unknown compounds. The EPA has identified target analytes that are of health concern which need to be captured by the tubes; however, these sites contain other compounds which are not regulated. Thus, these unknown compounds may interfere with the analysis or may not be detected using current tube designs. The sorbent devices described herein can be placed in or above the soil for a desired time to permit diffusion of species into the sorbent device. The device can then be removed and analyzed using, for example, thermal desorption analysis.

In certain examples, an illustration of a sorbent device is shown in FIG. 1. The sorbent device 100 includes a sampling inlet 110, a base 120, which is referred to in some instances herein as a sampling outlet, and a longitudinal diffusion path 130 between the sampling inlet 110 and the base 120. The terms inlet and outlet are used for convenience purposes only and are generally described in reference to the order of the sorbent materials in the sorbent device 100. For example, the sorbent materials in the device are typically arranged from a material with a weakest sorbent strength to a material with a strongest sorbent strength with the weakest sorbent strength material adjacent to the sampling inlet. Such ordering provides several advantages including the ability to adsorb many different types of species using a single sorbent device. The terms stronger and weaker are relative terms, and the adsorption strength and desorption efficiency are functions of surface area, pore size(s) and shape(s), pore volume and surface chemistry of the sorbent materials. No absolute strength is required, rather the various materials that are used are stronger or weaker adsorbers relative to another material. It will be within the ability of the person of ordinary skill in the art, given the benefit of this disclosure, to select a material that is stronger or weaker than another material. Higher boiling point compounds are typically retained by the weaker sorbent materials, and the lighter analytes break through and are retained by the stronger sorbent materials. Thus, when compounds are adsorbed to the sorbent devices, the high boiling point materials would be located in sorbent material adjacent to the sampling inlet (or desorption outlet), and the low boiling point materials would be adsorbed on sorbent materials closer to the sampling outlet (or desorption inlet). Some even lighter components (like gases) break through and are retained by the strongest adsorbent immediately adjacent to the sampling outlet. The particular ordering of sorbent materials may be selected to increase the probability that all species adsorb and then desorb from the sorbent device. For example, it may be desirable to leave sites in the stronger sorbent material to be available to adsorb the lighter components. In addition, if the higher molecular weight analytes become adsorbed to the stronger or strongest sorbent material, they may not desorb. By permitting diffusion in one direction and desorbing in the opposite direction, the higher molecular weight materials do not occupy or enter into the stronger sorbent materials, which increases the likelihood that they will fully desorb from the sorbent device. As described herein, the sampling outlet is typically closed or sealed, at least for some part during the sampling procedure, such that fluid is permitted to diffuse into the device through the sampling inlet but not the base. For example, the area of the sorbent device 100 referred to as the base 120 can be closed or sealed such that air does not diffuse into the sorbent device 100 through the base 120. During analysis the base 120 can be opened such that a fluid carrier can be provided through the base to desorb species from the sorbent device 100.

In certain embodiments and in addition to the problems encountered with heavier hydrocarbon species, many lighter species can break through, e.g., may adsorb in only small quantities or not at all or may desorb too quickly, which can reduce the likelihood these species are detected at all or can lead to errors in quantitation. Also, many government regulations have decreased the detection limits required for soil vapor intrusion testing. Extending the sampling volume to decrease detection limits can cause a problem of break through for many lighter components when using available sampling devices. By including a series of sorbent materials with staggered strengths in the sorbent devices, the likelihood of break through can be reduced.

Referring again to FIG. 1, the sorbent device 100 is shown as including two sorbent materials 140, 150 disposed generally on the inner surfaces of the body 105 of the sorbent device 100. The longitudinal fluid flow path 130 is fluidically coupled to each of the sorbent materials 140, 150 such that species that diffuse into the sorbent device 100 through the sampling inlet 110 can diffuse down the longitudinal fluid flow path 130 where they are adsorbed in one or both of the sorbent materials 140, 150. As discussed herein, the sorbent material 150 is typically a stronger sorbent material than the sorbent material 140. After the species are adsorbed, the sampling inlet 110 can be capped or covered, and the sorbent device 100 can be stored for future analysis or can be analyzed immediately using thermal desorption analyses as described herein. In some embodiments, at least one of the base and the sampling inlet comprises a coupling 160 configured to couple to the additional sorbent device. In other examples, a base cover 155 can be included.

In certain examples, the sorbent devices can include an air gap between the sampling inlet 110 and the sorbent material 140. While not required, the air gap may be desirable to balance out any air flows or, for example, buffer any sudden changes in concentration in the external sample and prevent spurious results. Where an air gap is present, the air gap may have a length of about 2 mm to about 30 mm, for example about 5 mm to about 35 mm, e.g., 10 mm, 15 mm or 20 mm.

In some examples, the sampling inlet can include a mesh, cap or other barrier if desired. The barrier can be fluid permeable such that, for example, sample fluid vapors can diffuse but not flow into the sorbent device. For example, a metal mesh can be present across the sampling inlet 110. This mesh can assist, for example, in preventing air movement within the air gap as a result of wind or the tube being carried so that only diffusive transfer of the molecules to the adsorbents occurs. This mesh may be permanent or may be present in the form of a cap that is coupled to the sampling inlet prior to use. Other configurations are also possible.

Figures 2A, 2B:
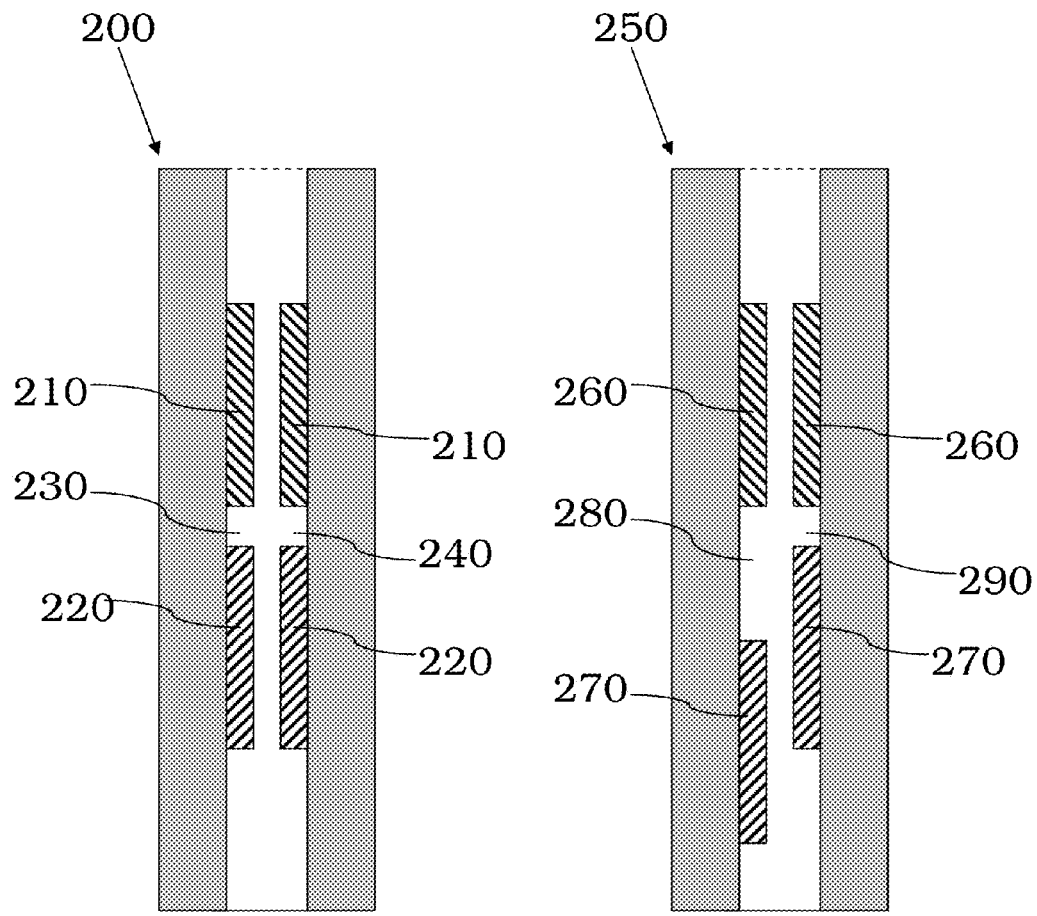
FIGS. 2A and 2B are illustrations of sorbent devices including void space between the sorbent materials, in accordance with certain examples.

In some examples, the sorbent devices described herein can be configured with one or more void spaces between the different sorbent materials. Referring to FIGS. 2A and 2B, a sorbent device 200 can include first and second sorbent materials 210, 220 having void spaces 230, 240 between the sorbent materials 210, 220. As shown in FIG. 2A, the void spaces 230, 240 can be substantially the same to facilitate easier deposition of the sorbent materials 210, 220 in the sorbent device. For example, a mask or spacer (not shown) can be inserted between sorbent materials 210, 220 to provide a void space between the sorbent materials 230, 240. In other examples, the void space may be unequal at different portions of the sorbent device. Referring to FIG. 2B, a sorbent device 250 can include first and second sorbent materials 260, 270 having void spaces 280, 290 between the sorbent materials 260, 270. As shown in FIG. 2B, the spacing of the void spaces 280, 290 are not the same. To create unequal spacing, some portion of one or more of the sorbent materials can be removed or otherwise not disposed in the sorbent device. For example, it may be desirable to have an unequal distribution of the sorbent materials in the device to increase or decrease adsorption at a particular area of the device.

Figure 3A:
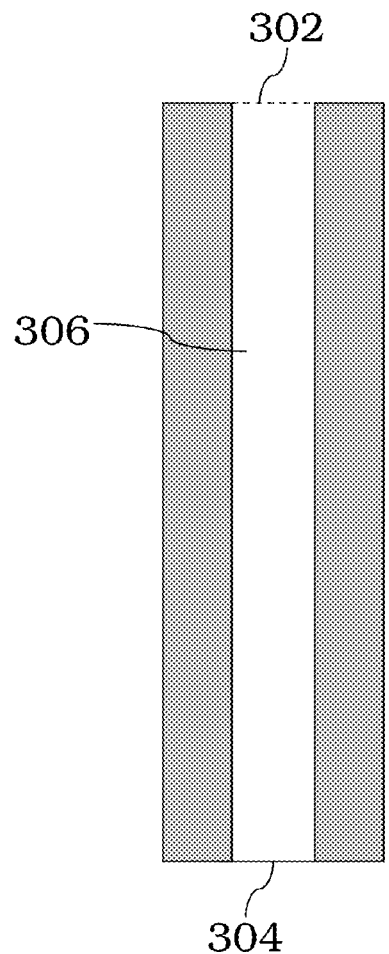
FIGS. 3A-3D are illustrations of sorbent devices including longitudinal diffusion paths with variable spacing, in accordance with certain examples.
Figure 3B:
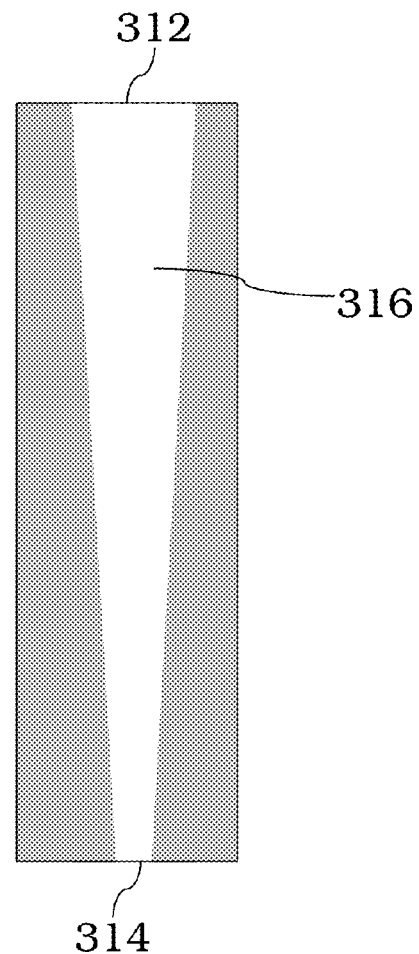
Figure 3C:
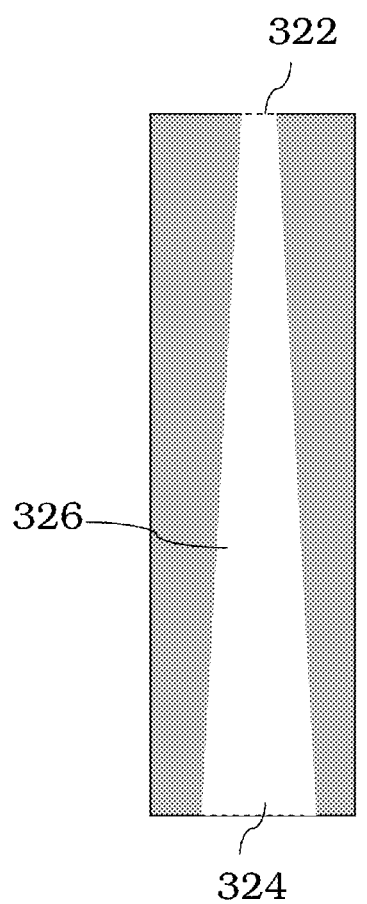
Figure 3D:
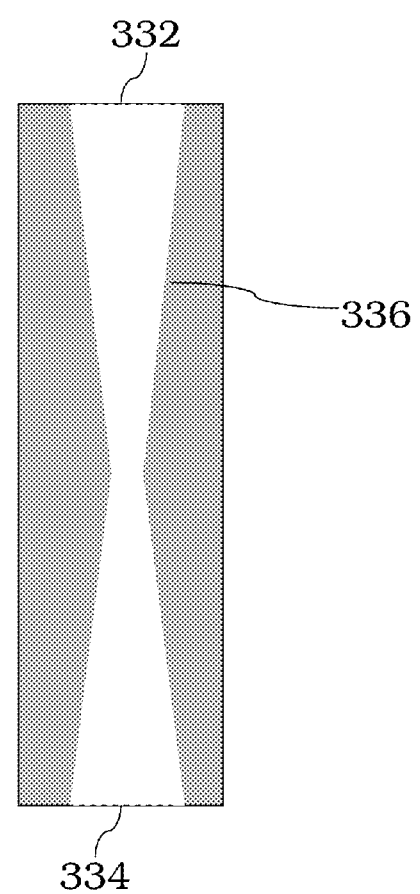

Notwithstanding that the sorbent device can include sorbent materials disposed within it in various manners, the longitudinal diffusion path of the sorbent device typically is open, at least to some degree, such that fluids such as gasses can flow into the different areas of the sorbent device through diffusional processes. Referring to FIG. 3A, a side view of a longitudinal diffusion path 306 is shown. The flow path 306 has substantially the same cross-sectional shape and diameter along the entire length of the flow path 306 from the sampling inlet 302 to the sampling outlet 304. The longitudinal diffusion path can also have a variable shape or cross-sectional diameter. Referring to FIG. 3B, a longitudinal diffusion path 316 has a greater cross-sectional diameter at a sampling inlet 312 than at base 314. Referring to FIG. 3C, a longitudinal diffusion path 326 has a smaller cross-sectional diameter at a sampling inlet 322 than at a base 324. Referring to FIG. 3D, a longitudinal diffusion path 336 has substantially the same cross-sectional diameter at a sampling inlet 332 and a sampling outlet 334, but the cross-sectional diameter along the length of the flow path varies. The embodiments shown in FIGS. 3A-3D are merely illustrative and other variable size longitudinal diffusion paths may be used in the sorbent devices described herein. As discussed further below, the particular shape and dimensions of the diffusion path can vary and may be selected, for example, based on the anticipated analytes that are present in a sample.

Figure 4A:
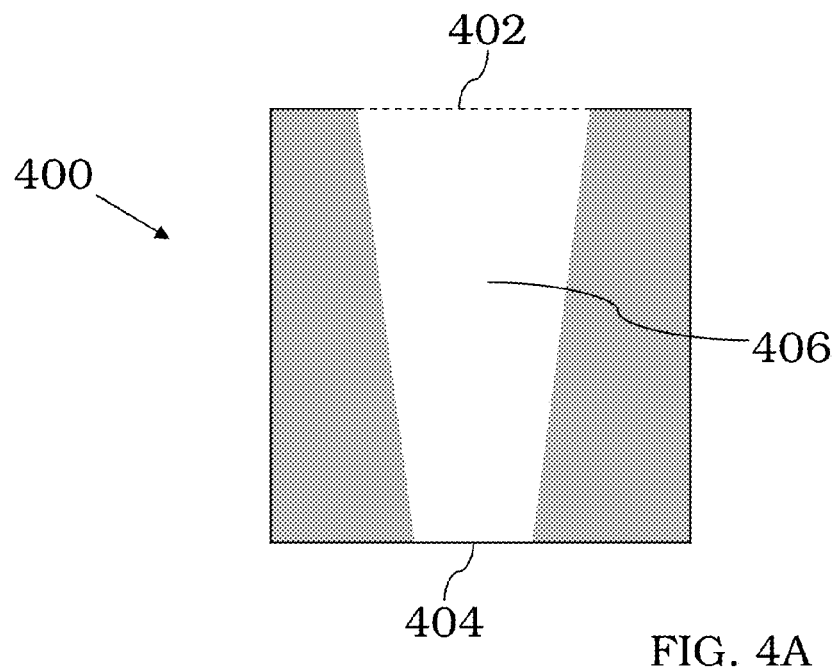
FIGS. 4A and 4B are illustrations showing that sorbent material can be disposed to provide a longitudinal diffusion path with a substantially constant cross-sectional diameter, in accordance with certain examples.
Figure 4B:
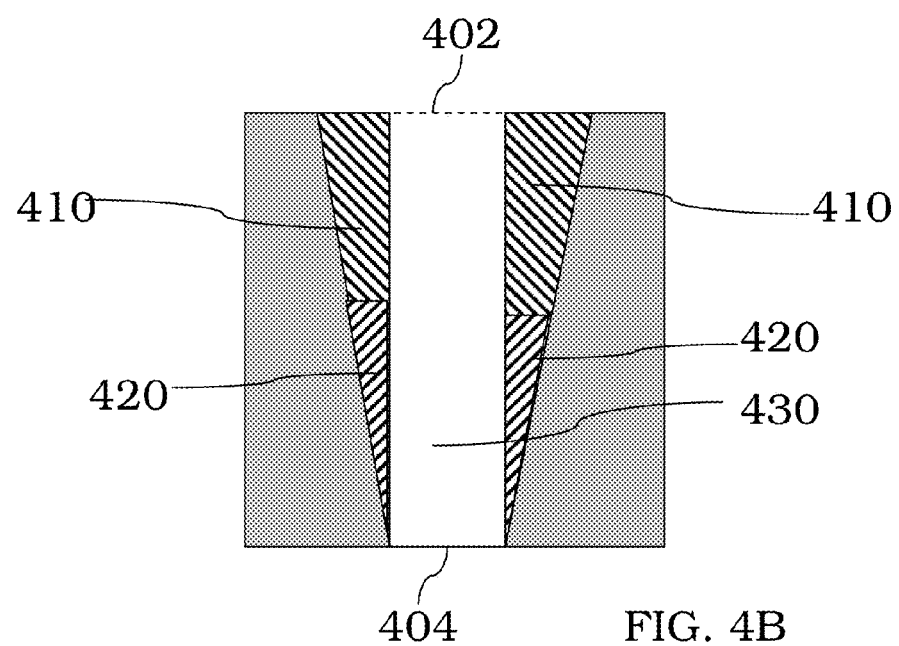

In certain embodiments, the diameter of the interior volume that forms the longitudinal diffusion path may be variable prior to disposition of any sorbent material in the interior but then have a substantially uniform channel after disposition of the sorbent material. For example and referring to FIGS. 4A and 4B, a sorbent device 400 is shown in FIG. 4A as including a variable size longitudinal diffusion path 406, with the diameter of the diffusion path 406 near a sampling inlet 402 greater than the diameter near a sampling outlet 404. Referring to FIG. 4B, after disposition of sorbent materials 410 and 420 in the sorbent device 400, a longitudinal diffusion path 430 is formed that has substantially the same cross-sectional diameter. In some examples, to form the longitudinal diffusion path 430, the sorbent material 420 can first be packed into the body of the sorbent device 400 to a desired depth. The sorbent material 410 can then be packed on top of the sorbent material 420 to a desired depth. A hole or channel can be drilled or machined into the packed sorbent materials 410, 420 to provide the longitudinal diffusion path 430. Other methods may also be used and are described in more detail herein.

In certain examples, the sorbent devices described herein can be produced by packing one or more sorbent materials in a suitable body. For example, the strongest sorbent material can be placed in a hollow tube and packed against a seal, mesh or other material adjacent to or in the sampling outlet. A second sorbent material can be placed directly on the first sorbent material, or a mesh, fluid permeable barrier or other material can be used to physically separate the two sorbent materials. A longitudinal diffusion path can then be drilled or machined into the disposed sorbent materials by producing a longitudinal channel through the disposed sorbent materials. If desired, the sampling inlet may include a mesh material or other desired material to assist in retention of the sorbent material in the sorbent device.

In other examples, a carrier, e.g., a sleeve, can be inserted into the longitudinal opening of the sorbent device, and sorbent material can be packed around the sleeve. If desired, one or more barriers, e.g., fluid permeable barriers, or other materials may be inserted onto the carrier to separate the sorbent materials. The carrier can then be removed to provide a longitudinal channel or opening, around which the sorbent material is packed, that is operative as a longitudinal diffusion path.

In some embodiments, the carrier may remain in place once the sorbent material is packed. If so, then the carrier may be porous or may be a mesh material such that fluid can flow between the longitudinal diffusion path and the sorbent material. In certain examples, the sorbent material may be packed between the sleeve and the body of the sorbent device, whereas in other examples, the sorbent material may be impregnated in or embedded, to at least some degree, in the carrier. Where a carrier is present, the carrier desirably includes one or more materials that can withstand the thermal desorption temperatures commonly used in thermal desorption analysis. In certain examples, the sorbent materials can be deposited on the carrier and then the assembly is inserted into the body of the sorbent device.

In certain examples, a fluid permeable barrier can be used to separate the various sorbent materials in the sorbent device. The fluid permeable barrier can also be used to retain the sorbent material in the sorbent device. For example, a fluid permeable barrier can be inserted into a hollow tube such that the strongest sorbent material will be disposed on the fluid permeable barrier near the sampling outlet. Alternatively, a non-permeable barrier can be placed at the sampling outlet such that diffusion of sample occurs in only one direction, e.g., from the sampling inlet to the sampling outlet. An additional fluid permeable barrier can be placed on the deposited first sorbent material to separate it from the second sorbent material. This process can be repeated until a desired amount and type of sorbent materials have been deposited in the sorbent device. At the sampling inlet of the sorbent device, a mesh, clip or other retention device can be placed to hold the sorbent materials in the sorbent device.

In other examples, the sorbent materials can be chemically bonded to the inner surface of the body of the sorbent device. Such bonding may occur using techniques commonly employed in the manufacture of porous open layer tubular columns or solid phase micro extraction columns. Other techniques such as gas deposition, vapor deposition or the like can also be used to deposit the materials in the sorbent devices.

In certain embodiments, more than two materials can be used in a sorbent device. For example, it may be desirable to include three, four, five, six, seven or more types of sorbent materials within the sorbent devices to facilitate analysis of a plurality of species in a sample. The number of sorbent materials used in the sorbent devices can vary depending on the number of analytes and the types of analytes suspected to be present. Where the number and type of analytes are unknown, a sorbent device including a plurality of different types of sorbent materials can be used to ensure that substantially all of the analytes can be analyzed. In one embodiment where four or more sorbent materials are used, the sorbent materials can be arranged from weakest to strongest with the weakest sorbent material being closest to the sampling inlet and the strongest sorbent material being closest to the sampling outlet.

In certain examples, it may be desirable to include a particular sorbent material in a larger amount that the other sorbent materials. For example, where a sample is suspected of having a large concentration of a particular analyte, the sorbent material effective to adsorb and desorb that analyte may be present in a larger amount/volume to provide for increased loading of that analyte. The amount of the analyte can be increased or the surface area accessible to the analyte can be increased to assist in increased adsorption of that analyte to the sorbent device. Alternatively, it may be desirable to include more of the stronger sorbent materials to increase the overall likelihood that highly volatile compounds will adsorb to the sorbent device.

Figure 5A:
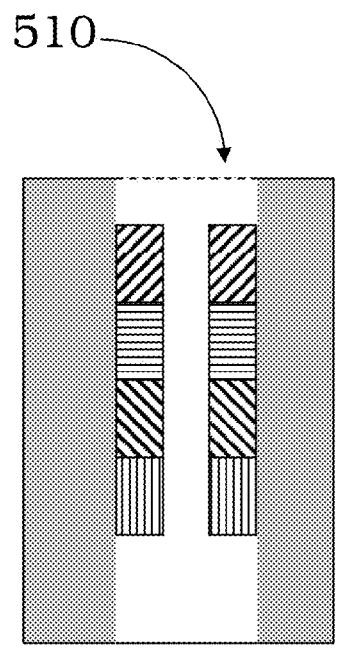
FIGS. 5A-5C are illustrations of sorbent devices including three, four or five different sorbent materials, in accordance with certain examples.
Figure 5B:
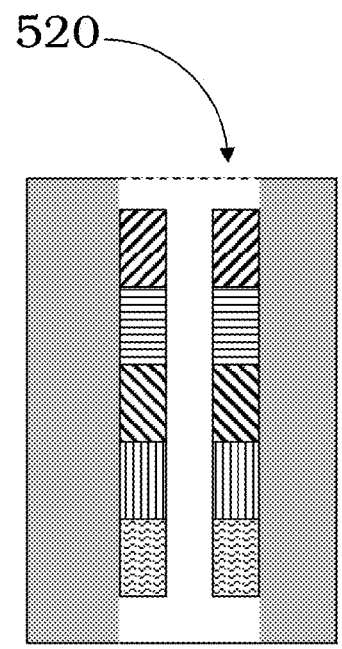
Figure 5C:
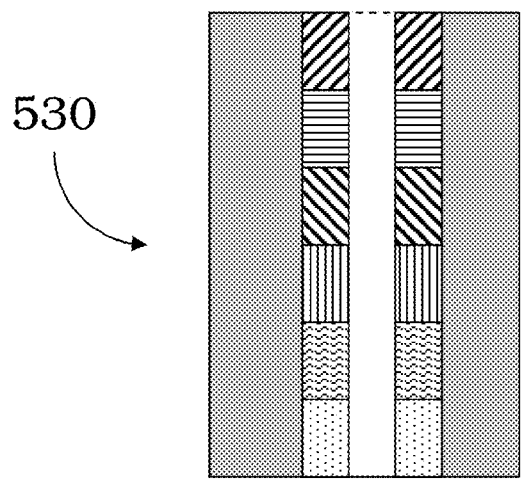

In certain embodiments and as described herein, the exact number and type of sorbent materials present in the sorbent device can vary and may include, for example, two, three, four, five, six or more. Illustrative examples of a sorbent device 510 that includes four sorbent materials, a sorbent device 520 that includes five sorbent materials and a sorbent device 530 that includes six sorbent materials are shown in FIGS. 5A-5C, respectively. These illustrative devices can include a carrier, or if desired, the carrier can be absent. While the devices shown in FIGS. 5A-5C are shown as lacking void space between the different sorbent materials, void spaces, which may have the same or different spacing, may be present if desired. In addition, it may be desirable to increase the overall length of the sorbent device to accommodate additional sorbent materials.

In certain examples, the sorbent materials can each be present at substantially the same weight ratio, e.g., 1:1. In other examples, the different sorbent materials can independently be present in weight ratios ranging from 3:1, 2.5:1, 2:1, 1.5:1, 1.1:1, 0.9:1, 0.8:1, 0.7:1, 0.6:1, 0.5:1, 0.4:1, 0.3:1, 0.2:1, 0.1:1 or any ratio in between these illustrative ratios. It may be desirable to determine the relative weight ratios using the first sorbent material (the one closest to the sampling inlet) as the normalization factor, and the amount of each of the other sorbent materials that is present can be divided by the amount of the first sorbent material that is present to determine the relative weight ratios present in the sorbent device. Additional suitable amounts of the sorbent materials will be readily selected by the person of ordinary skill in the art, given the benefit of this disclosure.

Figure 6A:
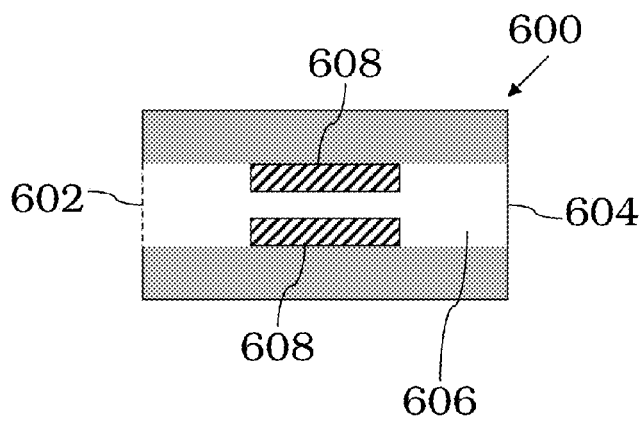
FIGS. 6A and 6B are illustrations of pluggable sorbent devices and FIG. 6C is an illustration showing the coupling of the devices of FIGS. 6A and 6B, in accordance with certain examples.
Figure 6B:
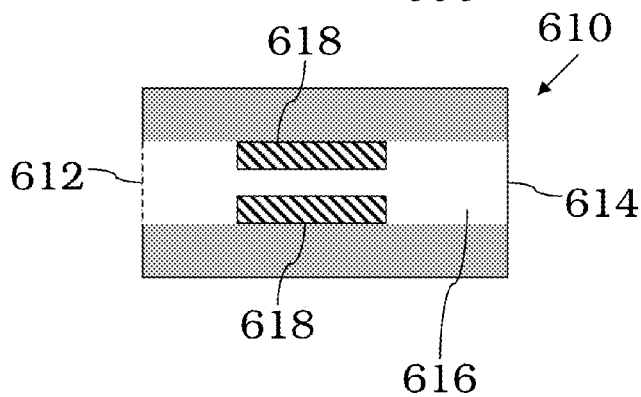
Figure 6C:
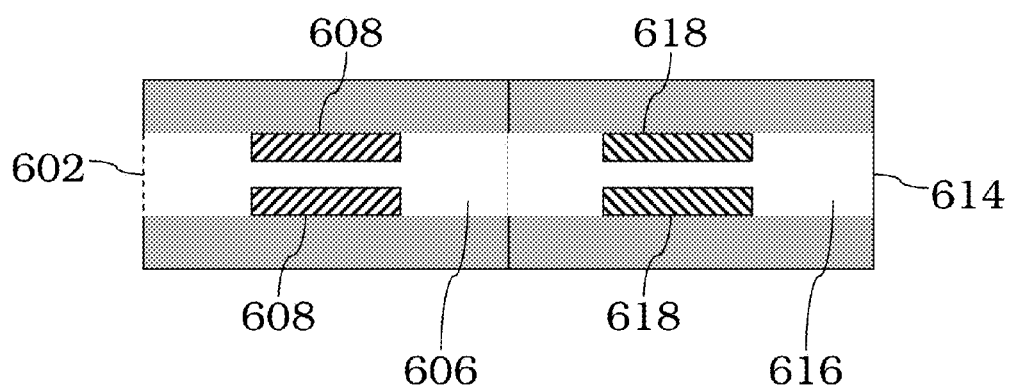
Figure 7A:
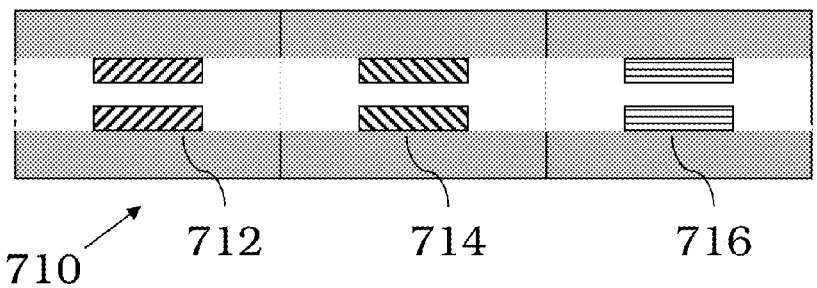
FIGS. 7A-7D are illustration of sorbent devices formed from coupling pluggable sorbent devices, in accordance with certain examples.
Figure 7B:
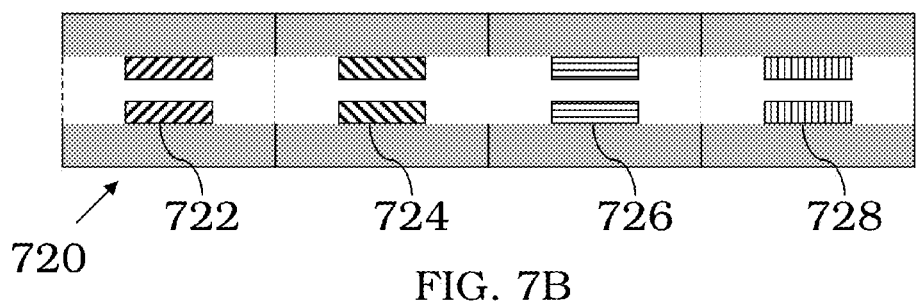
Figure 7C:
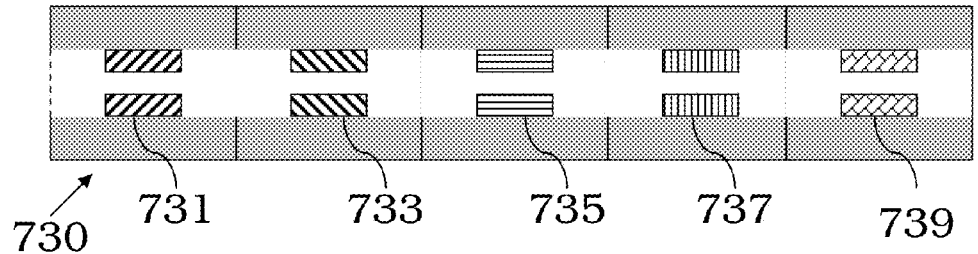
Figure 7D:
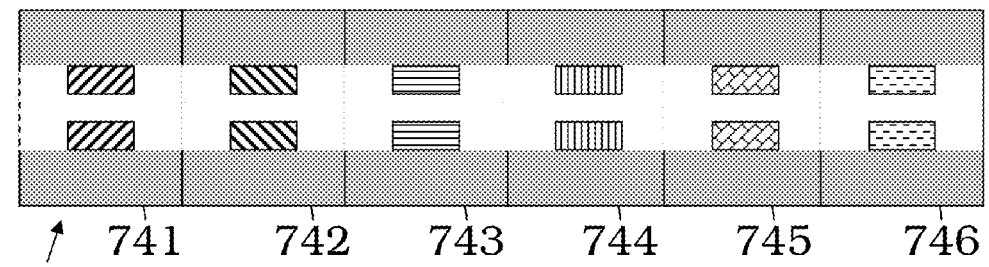

In certain embodiments, the sorbent materials may be individually packed into sorbent devices that can be fluidically coupled to each other to provide a pluggable sorbent device. For example and referring to FIGS. 6A-6C, a first sorbent device 600 can include a sampling inlet 602, a base 604 and a longitudinal diffusion path 606 between the inlet 602 and the base 604. A first sorbent material 608 is shown as being present in the first sorbent device 600. A second sorbent device 610 can include a sampling inlet 612, a base 614 and a longitudinal diffusion path 616 between the inlet 612 and the base 614. A second sorbent material 618 is shown as being present in the second sorbent device 610. The two sorbent devices can be plugged into each other or otherwise coupled by coupling the base or sampling outlet 604 of the first sorbent device 600 to the sampling inlet 612 of the second sorbent device 610. In this manner, the longitudinal diffusion paths 606 and 616 become fluidically coupled to each other as shown in FIG. 6C. Depending on the strength of the sorbent materials relative to each other, it may be desirable to instead couple the devices by coupling the sampling outlet 614 of the second sorbent device 610 to the sampling inlet 602 of the first sorbent device 600. Such pluggable sorbent devices provide increased flexibility as a user can decide the particular type, order and number of sorbent materials that can be present. For example, a user may piece together a selected number of pluggable sorbent devices on-site to analyze an air sample. Such flexibility is desired particularly where an environment may include a large number of analytes in a sample. In some examples, two, three, four, five, six or more pluggable devices, each including a different sorbent material, can be coupled to each other to provide a sorbent device. Illustrations of sorbent devices including three, four, five and six individual pluggable sorbent devices that are shown as devices 710, 720, 730 and 740, respectively, in FIGS. 7A-7D, respectively. For example, device 710 includes sorbent materials 712, 714 and 716, device 720 includes sorbent materials 722, 724, 726 and 728, device 730 includes sorbent materials 731, 733, 735, 737 and 739 and device 740 includes sorbent materials 741, 742, 743, 744, 745 and 746. The pluggable sorbent devices may include one or more fittings to provide a substantially tight fluid seal between the sorbent devices when coupled. For example, threads, gaskets, washers or the like can be included to effectuate coupling and the provision of a fluid tight seal between different pluggable sorbent devices.

Figure 8:
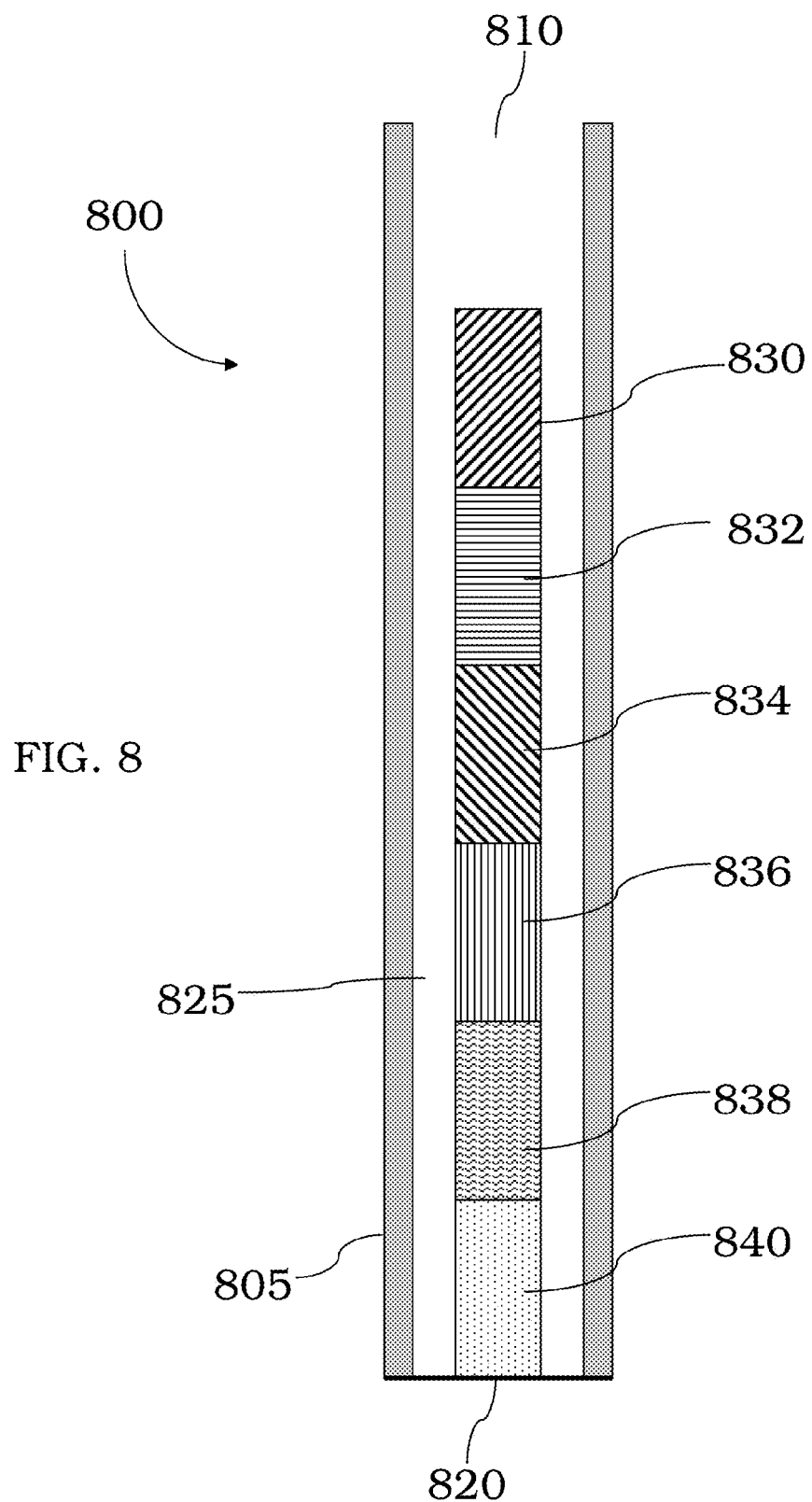
FIG. 8 is an illustration of a sorbent device including an inner arrangement of sorbent materials, in accordance with certain examples.
Figure 9:
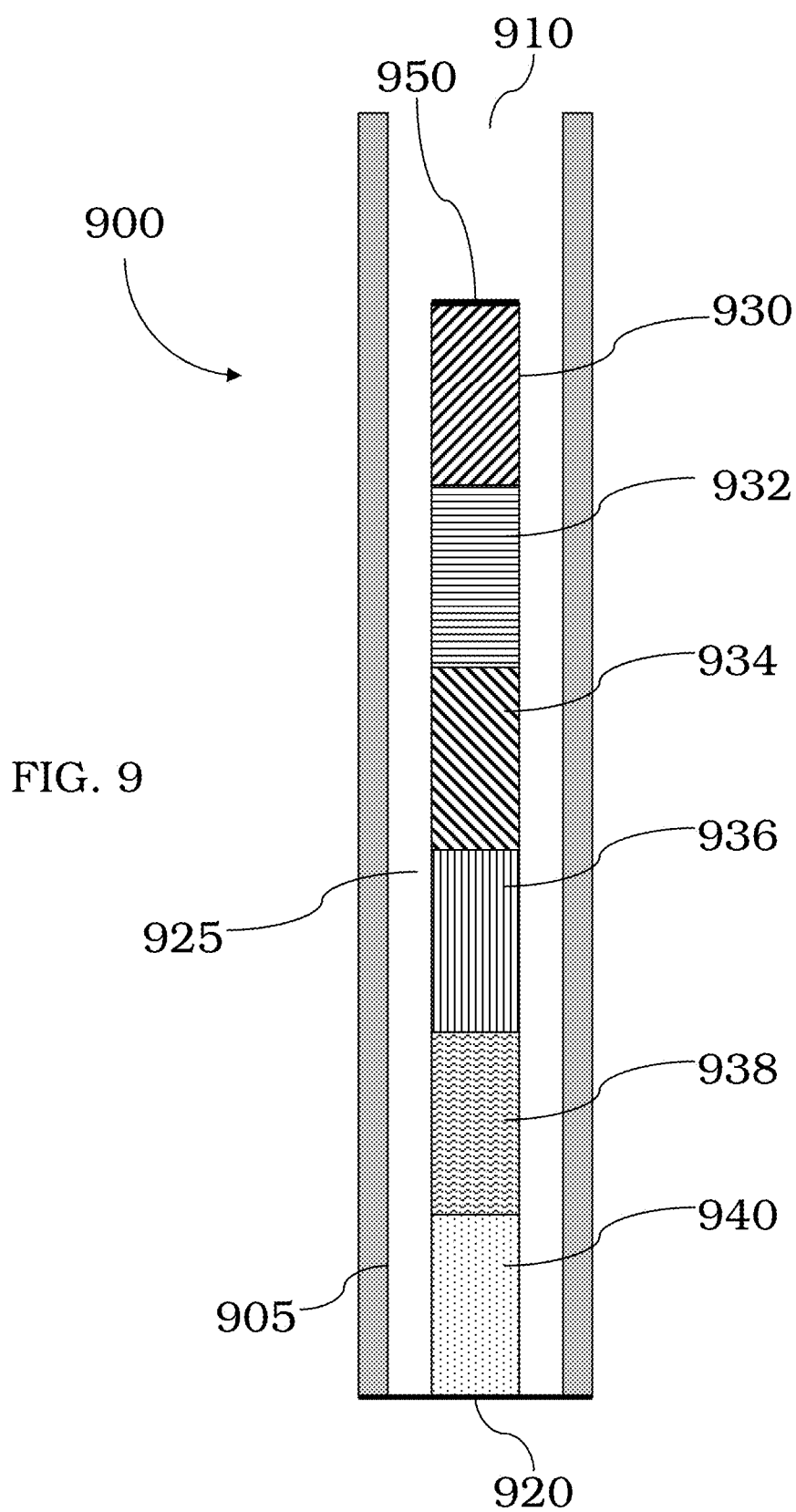
FIG. 9 is an illustration of a sorbent device including an inner arrangement of sorbent materials and including a material coupled to the sorbent material adjacent to the sampling inlet, in accordance with certain examples.

In certain examples, the sorbent materials need not be disposed against the inner walls of the sorbent devices. In some examples, the sorbent materials can be disposed in an interior portion of the sorbent device to permit diffusion of sample around the sorbent materials. For example and referring to FIG. 8, a sorbent device 800 includes a plurality of sorbent materials 830, 832, 834, 836, 838 and 840 deposited substantially concentrically within a body 805 of the sorbent device 800. The sorbent device 800 also includes a sampling inlet 810 and a base or sampling outlet 820. While not shown, the sorbent device can include, if desired, radial arms or radial support structures to retain the sorbent media within the sorbent device. The packing configuration shown in FIG. 8 permits the use of a longitudinal diffusion path 825 between the walls of the body 805 of the sorbent device 800 and the packed sorbent materials 830-840. As shown in FIG. 8, the top of the sorbent device 810 is open in that no barrier or mesh is present. If desired, the top sorbent material can include a mesh or other material to prevent fluid flow into the top of the sorbent material. For example and referring to FIG. 9, a sorbent device 900 includes a plurality of sorbent materials 930-940 with the weakest sorbent material 930 nearest a sampling inlet 910 and the strongest sorbent material 940 near the base or sampling outlet 920. A longitudinal diffusion path 925 exists around the sorbent materials 930-940. A mesh or barrier 950 can be deposited on the sorbent material 930 if desired to assist, for example, in proper diffusion of the sample species around the sorbent materials 930-940.

Figure 10:
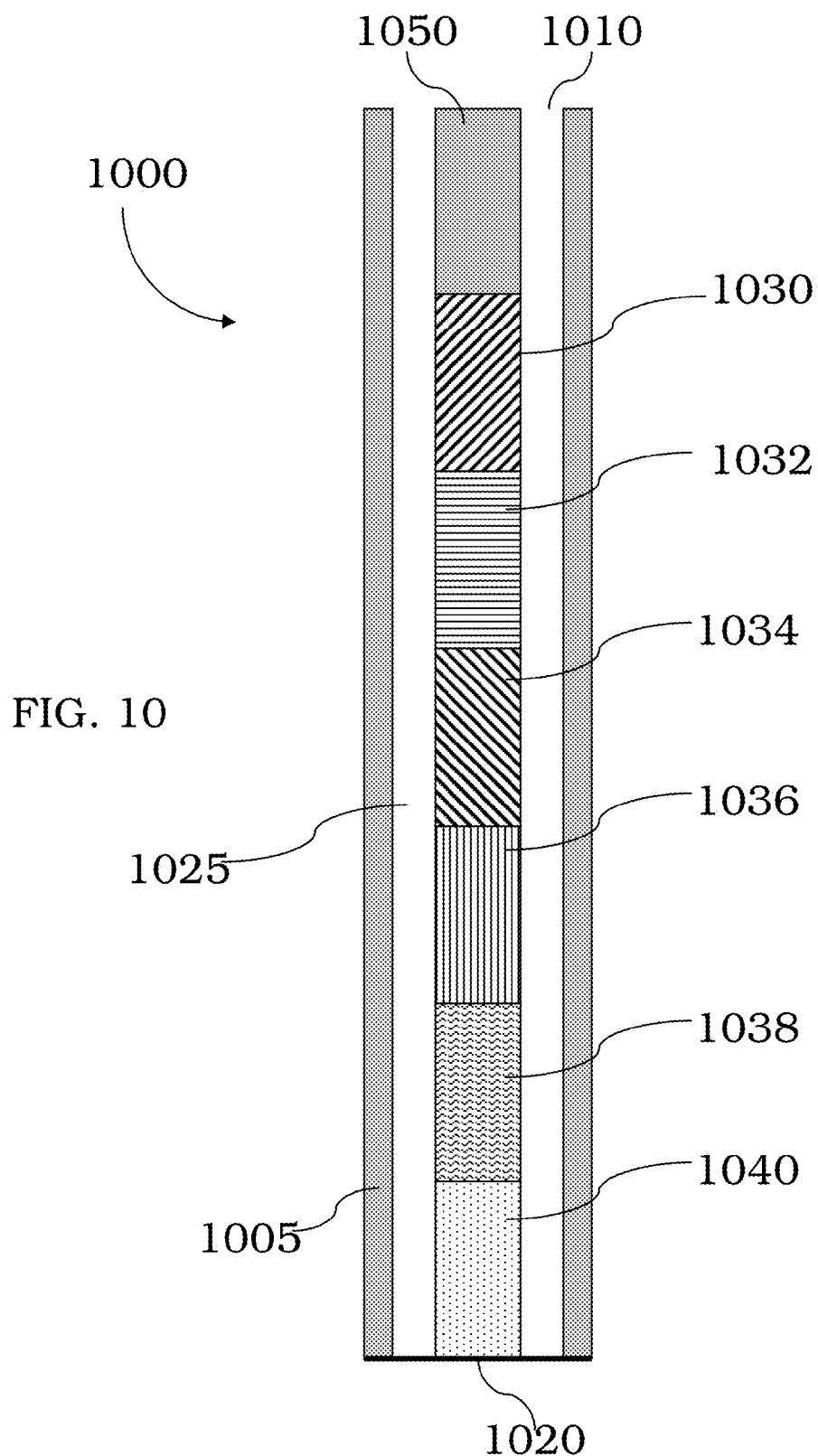
FIG. 10 is an illustration of a sorbent device including a non-adsorbing material to the sorbent material nearest to the sampling inlet, in accordance with certain examples.

In certain embodiments, it may be desirable to provide a non-adsorbing material on the top of the sorbent materials. For example and referring to FIG. 10, a sorbent device 1000 is shown as including a plurality of sorbent materials 1030, 1032, 1034, 1036, 1038 and 1040 deposited substantially concentrically within a body 1005 of the sorbent device 1000. The sorbent device 1000 also includes a sampling inlet 1010 and base or a sampling outlet 1020. The configuration shown in FIG. 10 permits the use of a longitudinal diffusion path 1025 between the walls of the body 1005 of the sorbent device 1000 and the packed sorbent materials 1030-1040. A non-adsorbing material 1050 can be present and adjacent to the sorbent material 1030. The non-adsorbing material 1050 can provide, for example, a uniform air gap around the sorbent materials 1030-1040. If desired, a mesh or other barrier can be present between the non-adsorbing material 1050 and the sorbent material 1030. In some examples, the non-adsorbing material can take the form of a cap, spacer or other material.

In certain embodiments, the overall length of the sorbent device can vary from about 50 mm to about 120 mm, e.g., about 60 mm to about 100 mm or about 80-90 mm, for example about 88 mm. In certain examples, the sorbent material can occupy about 50-80% of the length of the sorbent device. For example, the sorbent material may occupy about 25-95 mm of the length of the sorbent device, e.g., about 45-70 mm or about 60 mm of the sorbent device length may include one or more sorbent materials. In some examples, the diameter of the sorbent device can vary from about 1 mm to about 10 mm, for example about 3 mm to about 8 mm, e.g., about 4-6 mm or about 5 mm. In some examples, the longitudinal diffusion path may have about the same length as the sorbent device or may have a shorter length.

Figure 11:
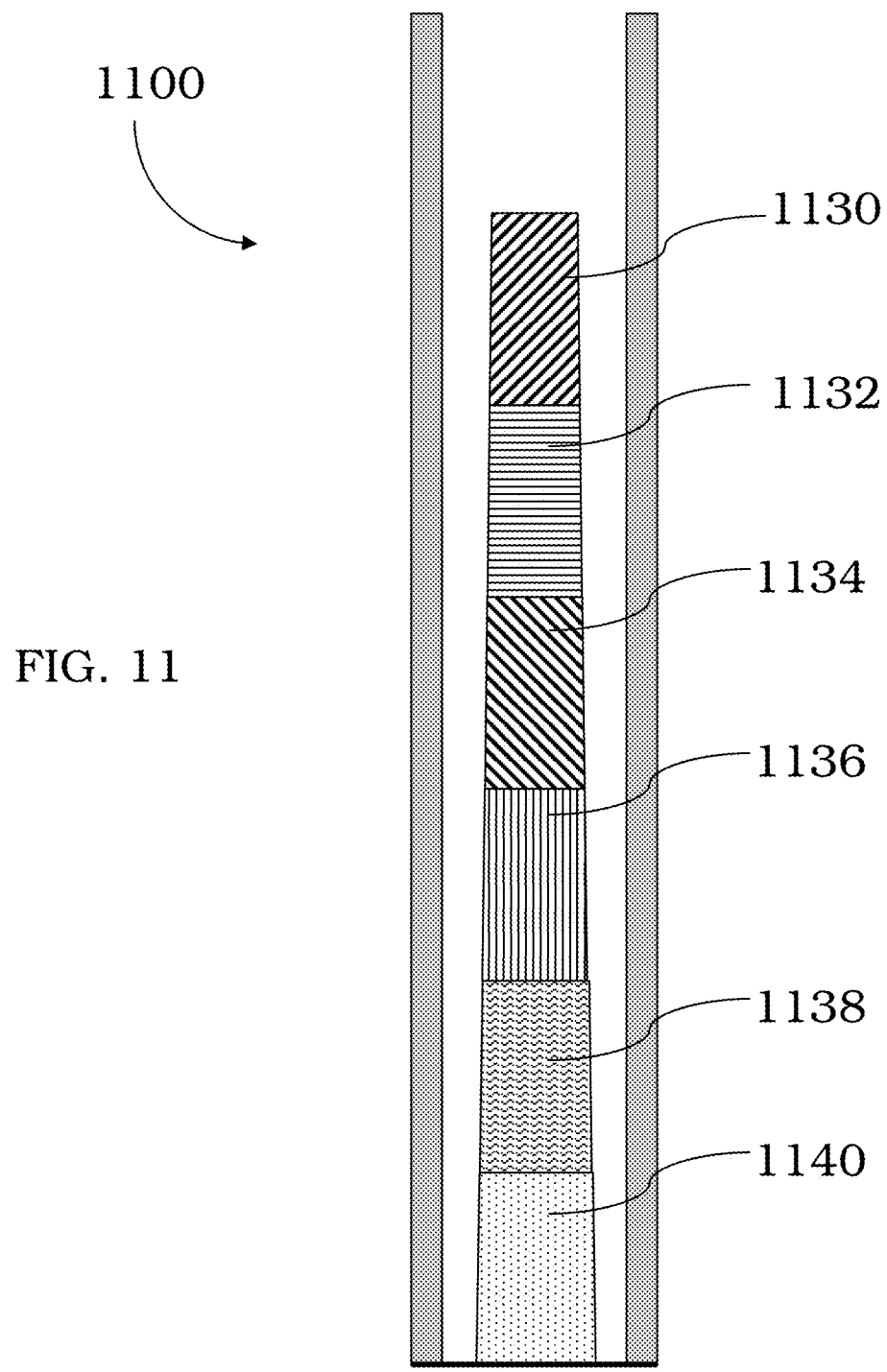
FIG. 11 is an illustration of a sorbent device including a tapered arrangement of sorbent materials, in accordance with certain examples.

In some examples where the sorbent materials are disposed within the interior of the sorbent device, the shape and configuration of the sorbent materials can be different from other sorbent materials in the device. For example and referring to FIG. 11, a sorbent device 1100 is shown as including a plurality of sorbent materials 1130-1140. The sorbent materials 1030-1040 are tapered in that the diameter of the sorbent material 1140 is greater than the diameter of the sorbent material 1130. The tapering could be reversed or the tapering could have a symmetric axis such that the inner sorbent materials have less diameter than the top and bottom sorbent materials. Other configurations are also possible including, for example, where the sorbent tapering is combined with tapering of the interior channel of the body of the sorbent device. In particular, depending on the desired diffusional characteristics of the sorbent device, the particular configuration of the sorbent materials and longitudinal diffusion path can be varied.

In embodiments that employ an internal arrangement of sorbent materials, e.g., those illustrative embodiments shown in FIGS. 8-11, the sorbent materials can be disposed in the devices in numerous manners. In one example, a hollow sleeve can be inserted into the sorbent device and the materials can be added to the interior of the hollow sleeve. Once packed, the hollow sleeve can be removed to provide the longitudinal diffusion path around the packed sorbent materials. In other examples, the sorbent device can be packed and material adjacent to the wall can be removed to provide a longitudinal diffusion path. In yet other examples, the sorbent materials can be disposed in a first tube and then removed and inserted into a different tube having a larger diameter such that a longitudinal diffusion path exists between the sorbent material and the inner wall of the sorbent device. These methods are illustrative of suitable methods for disposing sorbent materials, and additional suitable methods will be readily selected by the person of ordinary skill in the art, given the benefit of this disclosure.

In certain embodiments, the sorbent materials may be arranged in a palindromic configuration with a sorbent device such that the sorbent materials are substantially symmetric about a central axis. For example and referring to FIG. 12, a sorbent device 1200 includes two sampling inlets 1210, 1220, and a longitudinal diffusion path 1230 between the inlets 1210, 1220. A first sorbent material 1240 is positioned adjacent to each of the sampling inlets 1210, 1220. A second sorbent material 1250 is positioned internally within the longitudinal diffusion path 1230 in the body 1205 of the sorbent device 1200. The first sorbent material 1240 has a weaker sorbent strength than the second sorbent material 1250. A minor plane is present in the central part of the body with respect to the ordering of the sorbent materials 1240, 1250. In this configuration, sample may be permitted to diffuse into each of the sampling inlets 1210, 1220. After sampling, the sorbent device can be analyzed by introducing a carrier gas into the sorbent device 1200. If desired, the sorbent device can be broken or cut into two or more pieces such that carrier gas can be introduced in an opposite direction from the direction of sample diffusion into the sorbent device 1200.

Figure 13:
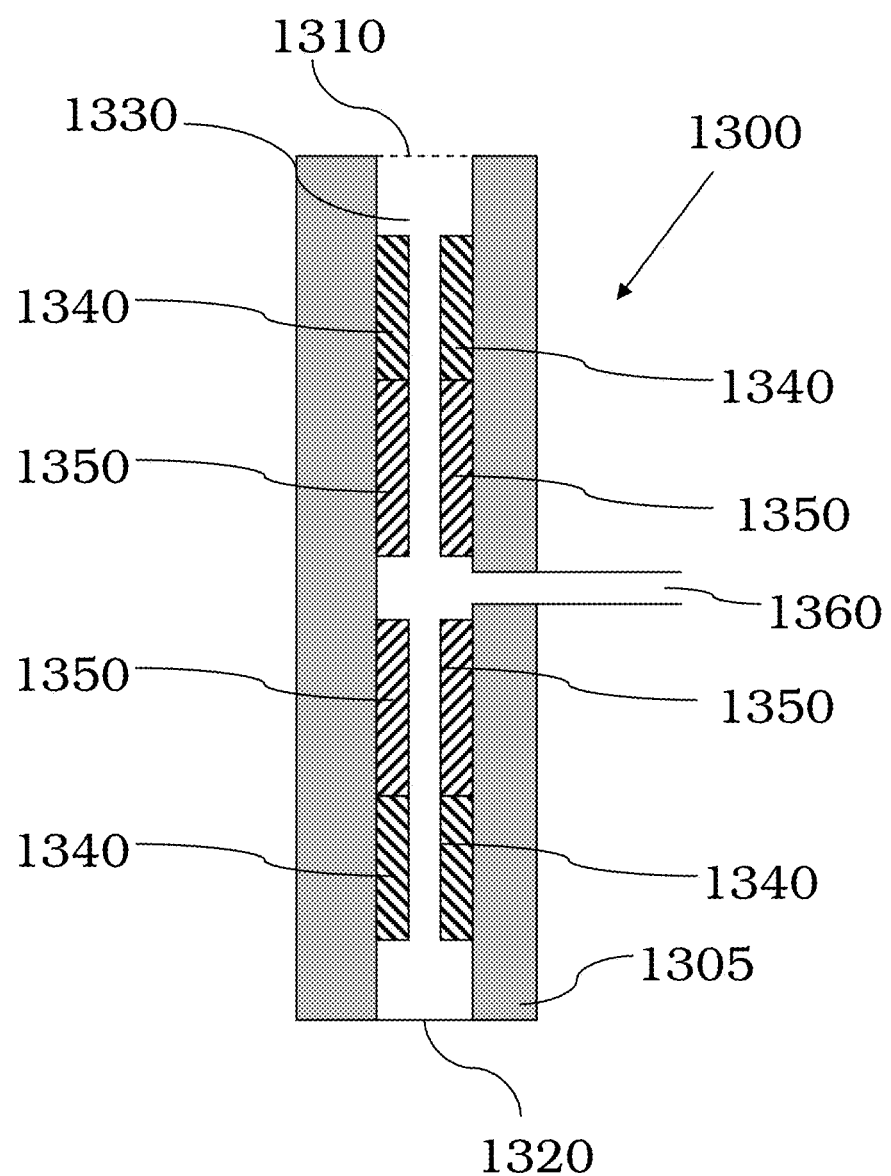
FIG. 13 is an illustration of a sorbent device including a palindromic arrangement of sorbent materials and a gas port, in accordance with certain examples.

In other examples, the sorbent device may include a gas port or the like at a central location on the sorbent device body. The gas port can be used to introduce a carrier gas into the sorbent device after sampling. One illustration is shown in FIG. 13. The sorbent device 1300 includes two sampling inlets 1310, 1320 and a longitudinal diffusion path 1330 between the inlets 1310, 1320. A first sorbent material 1340 is positioned adjacent to each of the sampling inlets 1310, 1320. A second sorbent material 1350 is positioned internally within the longitudinal diffusion path 1330 in the body 1305 of the sorbent device 1300. The first sorbent material 1340 has a weaker sorbent strength than the second sorbent material 1350. A gas port 1360 in the body 1305 can be present. During sampling the gas port 1360 is typically closed or sealed such that fluid does not diffuse into the device 1300 through the gas port 1360. When the sorbent device 1300 is being analyzed, a carrier gas can be introduced into the sorbent device 1300 through the gas port 1360 such that species can desorb from the sorbent materials 1340, 1350 and exit the sorbent device through the inlets 1310, 1320. It may be desirable to fluidically couple one or more chromatography columns to each of the inlets 1310, 1320 to separate species exiting the sorbent device 1300. A single chromatography column can be used or different chromatography columns can be coupled to each of the inlets 1310, 1320.

Figure 12:
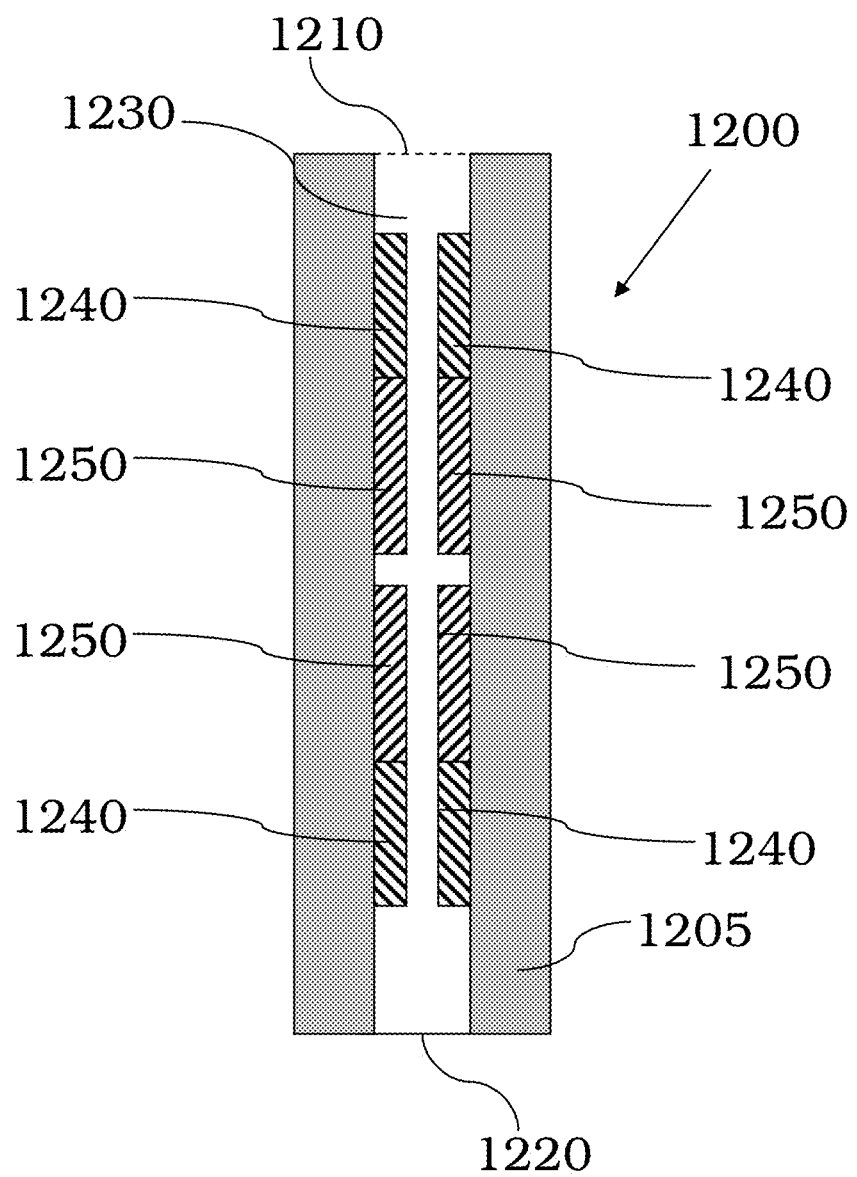
FIG. 12 is an illustration of a sorbent device including a palindromic arrangement of sorbent materials, in accordance with certain examples.

While the palindromic arrangement shown in FIGS. 12 and 13 includes two different sorbent materials, three, four, five, six or more sorbent materials may instead be arranged in a similar manner. In addition, the sorbent materials can be tapered or otherwise present in different amounts or configurations in the palindromic sorbent devices described herein. In some examples, the palindromic configuration may include sorbent materials disposed on the inner surfaces of the sorbent device, whereas in other palindromic configurations, the sorbent materials may be concentrically disposed similar to those configuration shown, for example, in FIGS. 8-11. In addition, pluggable sorbent devices can be coupled in a suitable manner to provide a palindromic configuration of sorbent materials in the coupled device.

In certain embodiments, one or more of the sorbent material types used in the sorbent devices described herein may be based on, or include, one or more of charcoal, carbon blacks (e.g., e.g. CarboTrap™ and CarboPack™ products), carbon-molecular sieves (e.g., CarboSieve™ and Carboxen™ products), porous polymers (e.g., Tenax™, Porapak™, HayesSep™ products), silicones (e.g., polydimethylsiloxane (PDMS)), molecular sieves, silica gels or may include other materials.

In some examples, the sorbent material can be a graphitized carbon black, a carbon molecular sieve, or combinations thereof. In some examples, the sorbent material may be include, or be based on a mixture of, graphitized carbon blacks of different strengths, graphite, carbon molecular sieves, polymer resins, an oxide, fused silica beads, glass, quartz, charcoal, porous polymers, amisorbs or other materials. In certain embodiments, the different sorbent material in the sorbent devices may have a different chemical composition, e.g., each may include or be a different carbon black. In some examples, the sorbent material may be a derivatized form, e.g., a derivatized carbon black.

In some examples, the sorbent material can be a graphitized carbon black such as, for example, Carbotrap™ B sorbent or Carbopack™ B sorbent, Carbotrap™ Z sorbent or Carbopack™ Z sorbent, Carbotrap™ C sorbent or Carbopack™ C sorbent, Carbotrap™ X sorbent or Carbopack™ X sorbent, Carbotrap™ Y sorbent or Carbopack™ Y sorbent, Carbotrap™ F sorbent or Carbopack™ F sorbent, any one or more of which may be used in its commercial form (available commercially from Supelco or Sigma-Aldrich) or may be graphitized according to known protocols. In other examples, the sorbent material can be carbon molecular sieves such as Carboxen™ 1000 sorbent, Carboxen™ 1003 sorbent, or Carboxen™-1016 sorbent, any one or more of which may be used in its commercial form (available commercially from Supelco or Sigma-Aldrich) or may be optimized according to known protocols. In certain embodiments where four different sorbent materials are present, each of the sorbent materials may be one of the sorbent materials listed in this paragraph with each of the sorbent materials being a different sorbent material than the other sorbent materials used in the sorbent device. In such instances, four different sorbent materials would be present in the sorbent device.

In certain examples, the mesh size or range of the sorbent can vary depending on the particular material selected. In some examples, the mesh size can range from 20 to about 100, more particular from about 20-80, 30-70 or 40-60. In other examples, the mesh size range may be from about 20-40, 40-60, 60-80 or 80-100 depending on the material used in the sorbent devices. Other suitable mesh sizes will be readily selected by the person of ordinary skill in the art, given the benefit of this disclosure.

In certain embodiments, the body of the sorbent device may be made from, or include, many different types of materials. In some examples, quartz, stainless steel, coated stainless steel or other metal or non-metal based materials that can tolerate the temperature cycles used to desorb the analytes can desirably be used.

In certain embodiments, the sorbent devices described herein can be used with automated thermal desorption (ATD) gas chromatography system. In one embodiment, ATD works by heating the sorbent device for a required amount of time to release volatiles from the sorbent material. During this heating, a carrier gas such as helium, nitrogen or hydrogen flows through the tube at a desired flow rate to transfer the contents of the sorbent tube onto a cooled secondary trap via a carrier gas, which is typically helium or hydrogen. This trap is then rapidly heated to desorb the collected components in a narrow band into the GC column for separation. A mass spectrometer is the most common detector used to provide the analysis. The information is sent to a computer containing an application which sends information to the instrument for control and collects information from the detector for analysis. This application has the ability to process this information which can provide quantitative and qualitative results.

By including many different types of sorbent materials in the sorbent devices, it may be possible to use a single desorption cycle to desorb substantially all adsorbed species. Such desorption typically permits reuse of the sorbent device without further temperature treatment, e.g., baking for extended periods, to remove high molecular weight species.

In certain embodiments, the sorbent devices described herein may be particularly advantageous for use where it is desirable to continuously monitor the air quality in an air space occupied by animals such as humans. For example, air may be periodically sampled in an airplane cabin, cockpit, spacecraft cabin, space station or the like for the presence of volatile species that may lead to adverse health effects.

Figure 14:
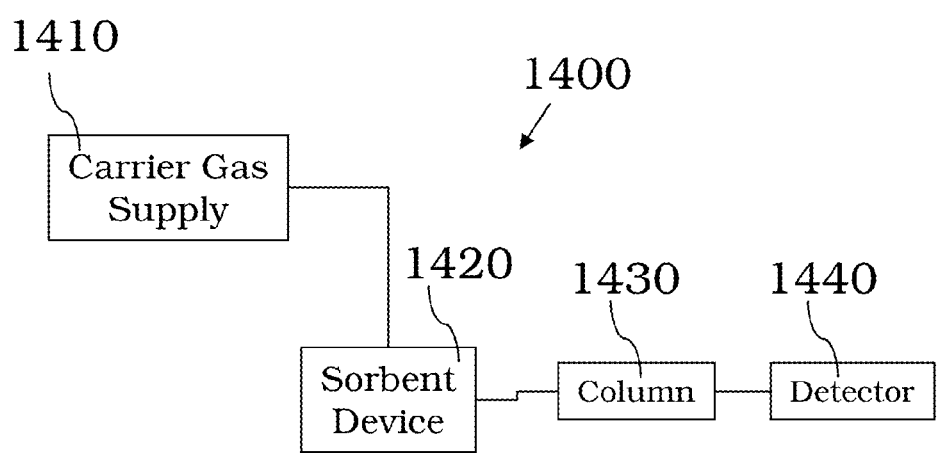
FIG. 14 is a schematic of a thermal desorption analyzer, in accordance with certain examples.

In certain examples, the sorbent devices described herein can be used with one or more instruments that are controlled or otherwise operated by, at least in part, a computer system. An illustrative system is shown in FIG. 14. The system 1400 includes a carrier gas supply 1410 fluidically coupled to a sorbent device 1420, which may be any of those described herein. Suitable valving or other devices may be present in the system to permit or restrict fluid flow between the carrier gas supply 1210 and the sorbent device 1420, depending on the desired flow of the carrier gas. In some examples, an injector may also be fluidically coupled to the sorbent device 1420 and/or carrier gas supply 1410, if desired. The sorbent device 1420 is fluidically coupled to a column 1430, which is effective to separate species based on their partitioning between the mobile phase and the column's stationary phase. Species that elute from the column 1430 are provided to a detector 1440, which can analyze those species based on chemical or physical properties. The detector can be any of those detectors commonly used in gas chromatographic systems including, but not limited to, a mass spectrometer, a flame ionization detector, a thermal conductivity detector, a thermionic detector, an electron-capture detector, a discharge ionization detector, a Hall electrolytic conductivity detector, an atomic emission detector, a flame photometric detector, a pulsed discharge ionization detector, a photoionization detector and other suitable types of detectors. In certain examples, the system 800 can include a computer system with a user interface such that a user may enter starting and final temperatures, temperature ramp parameters, sorbent device materials, and the like for use by the computer system in quantifying the analytes adsorbed to the sorbent devices. For example, in instances where a user already knows the particular set of analytes that are present, the user can select a previously entered chromatographic profile for use in the analysis. Other features for inclusion in a user interface will be readily selected by the person of ordinary skill in the art, given the benefit of this disclosure. In some examples, the sorbent devices described herein can be used with a swafer device such as those described in commonly assigned U.S. patent application Ser. No. 12/472,948 filed on May 27, 2009, the entire disclosure of which is hereby incorporated herein by reference for all purposes. In certain configurations where a swafer device is used, the carrier gas supply 1210 and the sorbent device 1220 can be fluidically coupled to different ports of the swafer device.

Figure 15:
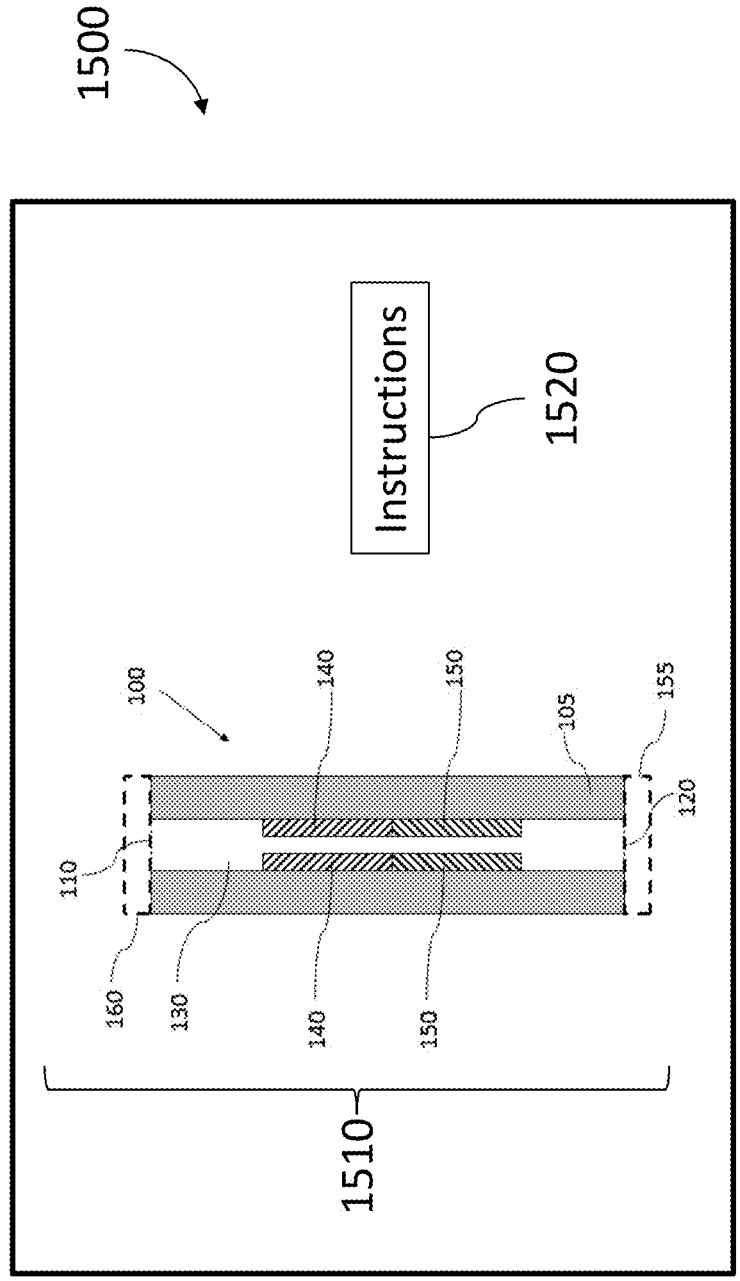
FIG. 15 is an illustration of a kit including a sorbent device and instructions, in accordance with certain examples.
Figure 16:
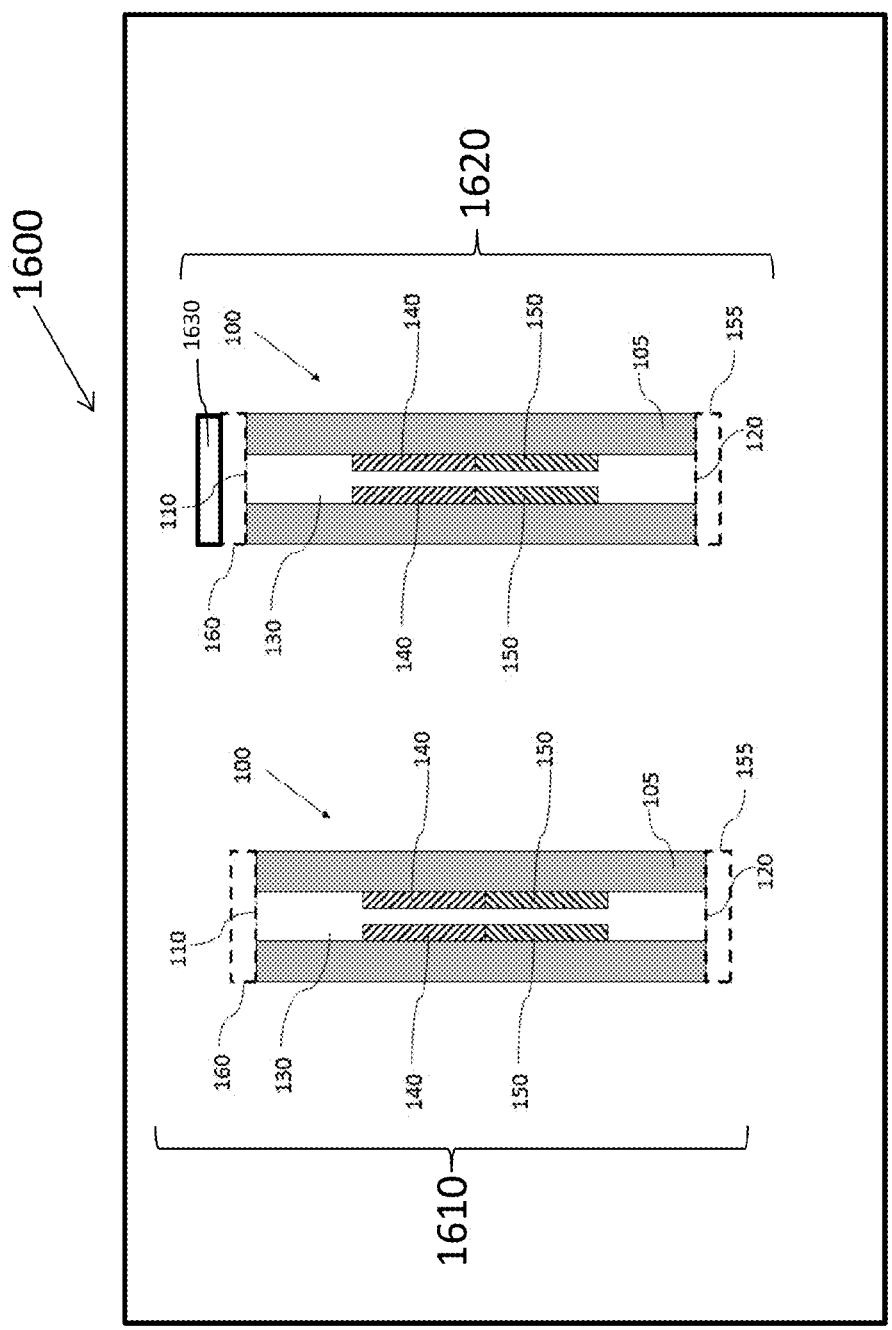
FIG. 16 is an illustration of a kit including two sorbent devices and an optional coupler, in accordance with certain examples.
Figure 17:
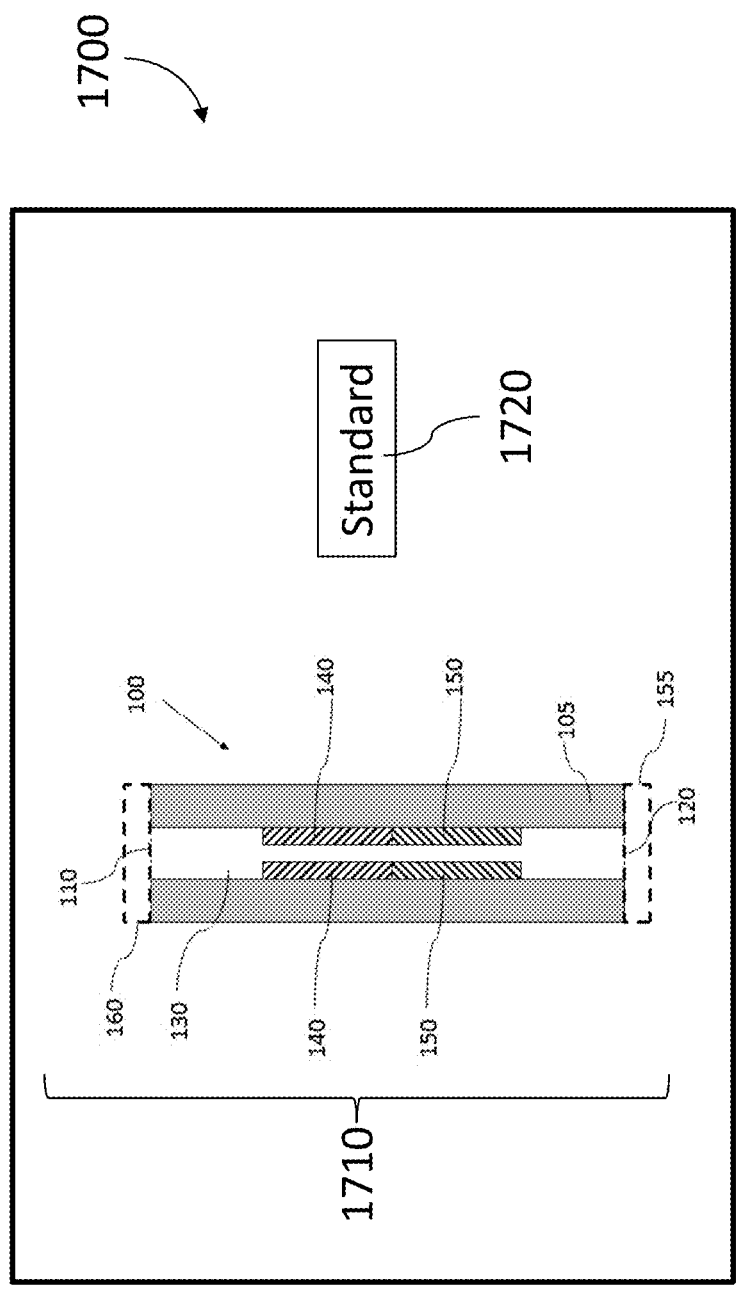
FIG. 17 is an illustration of a kit including a sorbent device and a standard, in accordance with certain examples.
Figure 18:
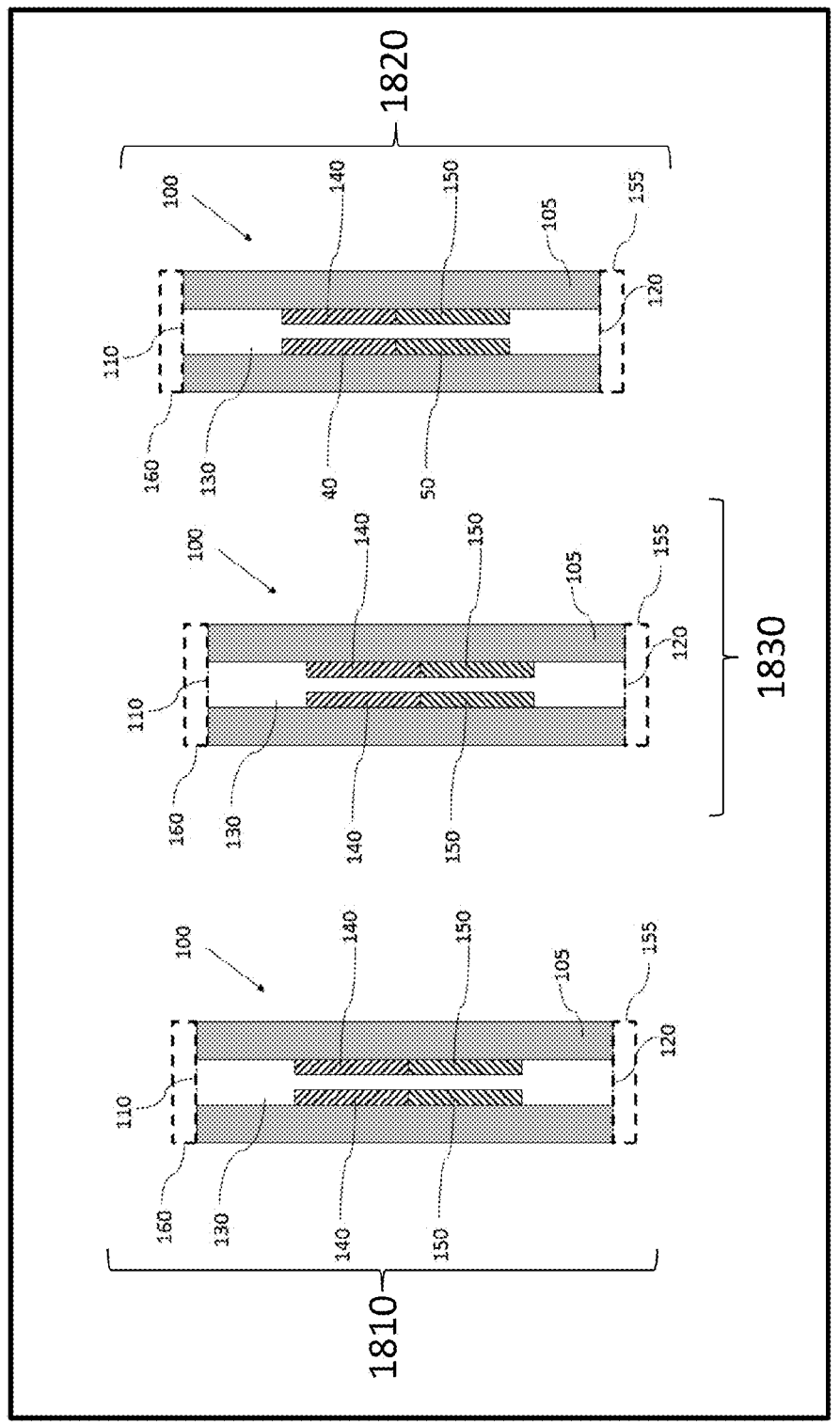
FIG. 18 is an illustration of a kit including a plurality of sorbent devices, in accordance with certain examples.
Figure 19:
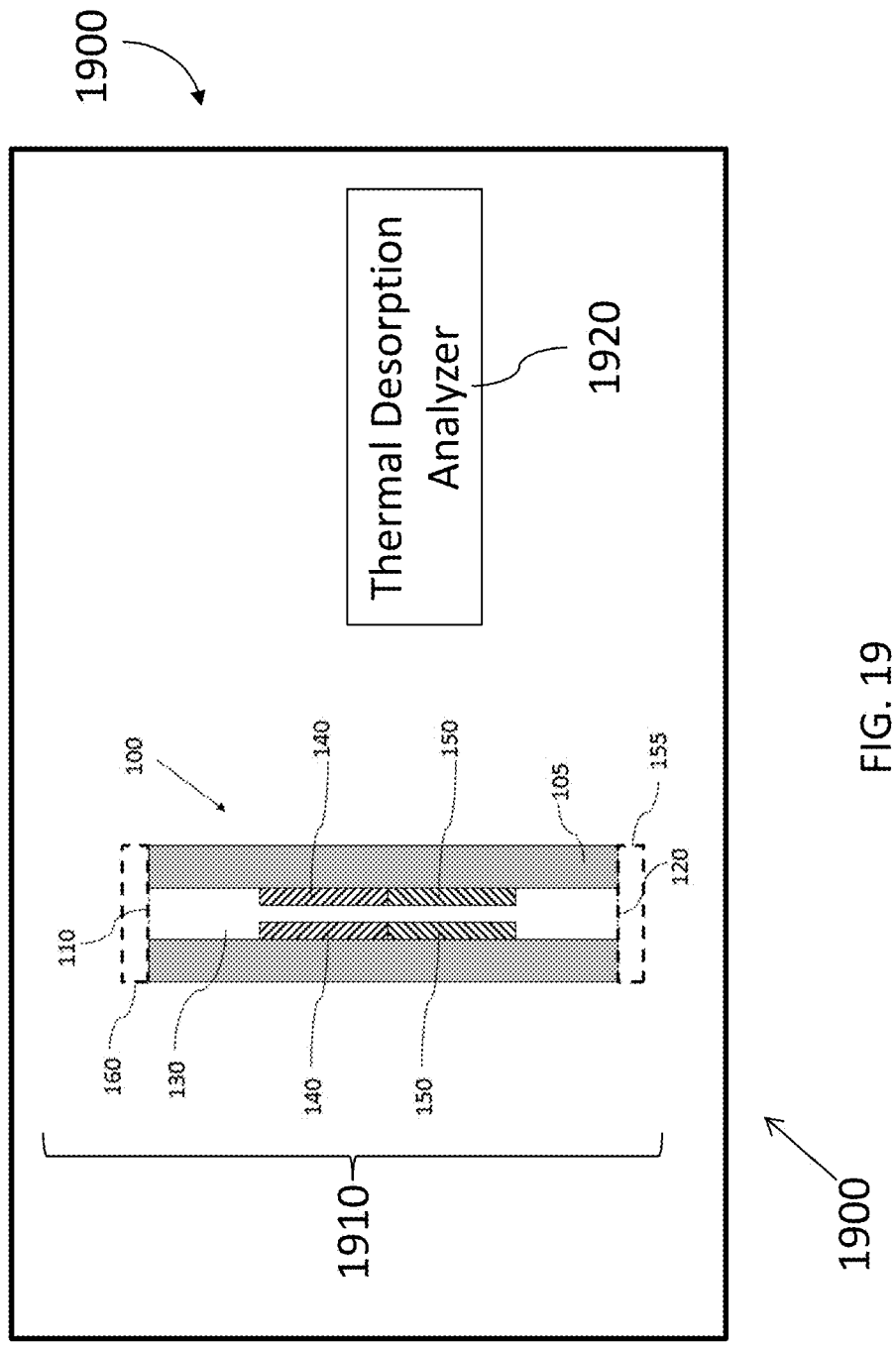
FIG. 19 is an illustration of a kit including a sorbent device and a thermal desorption analyzer, in accordance with certain examples.

In some examples, the sorbent device can be packaged in a kit optionally containing other components. For example and referring to FIG. 15, a kit 1500 may include one or more of the sorbent devices 1510 described herein optionally with other sorbent devices or instructions 1520. Where the sorbent device takes the form of a pluggable sorbent device, a plurality of pluggable sorbent devices (see sorbent devices 1810-1830 in the kit 1800 of FIG. 18) can be present each having a different sorbent medium such that an end-user can plug desired sorbent devices together to fluidically couple the longitudinal diffusion paths. The kit can also include other desirable components useful in sampling or analysis including, but not limited to, one or more standards (see FIG. 17 showing a kit 1700 including a standard 1720 in combination with a sorbent device 1710), caps, covers, fittings, couplings (see coupling 1630 in combination with sorbent devices 1610, 1620 in the kit 1600 of FIG. 16) or the like. In some examples and referring to FIG. 19, the kit 1900 can include a thermal desorption analyzer 1920 for use with the sorbent device 1910.

In certain examples, the sorbent devices described herein are useful for passive sampling of species by exposing a sorbent device to an environment comprising volatile species to permit volatile species in the environment to passively adsorb to the sorbent device. The adsorbed species can be subsequently desorbed to analyze the species present in the air sample. The particular sorbent materials used can vary and may be, for example, four different sorbent materials comprising a graphitized carbon black or may be a graphitized carbon black or a carbon molecular sieve with none of the materials being the same material.

In certain embodiments, a method of facilitating passive sampling of an air space comprising providing a sorbent device comprising a body comprising a sampling inlet, a sampling outlet and a longitudinal diffusion path between the sampling inlet and the sampling outlet, the sorbent device further comprising a serial arrangement of at least two different sorbent materials each fluidically coupled to the longitudinal diffusion path, in which the sorbent materials are arranged from a material with a weakest sorbent strength to a material with a strongest sorbent strength with the weakest sorbent strength material adjacent to the sampling inlet, in which the sorbent device is effective to adsorb volatile species in the air space to sample passively the air space can be used. The sorbent device can be any one or more of the sorbent devices described herein.

In other embodiments, a method of facilitating passive sampling of an air space comprising providing at least two pluggable sorbent devices can be performed. In some examples, a plurality of pluggable sorbent devices can be provided, e.g., three, four, five, six or more, to increase the number of configurations that are possible for the sorbent device.

When introducing elements of the aspects, embodiments and examples disclosed herein, the articles "a," "an," "the" and "said" are intended to mean that there are one or more of the elements. The terms "comprising," "including" and "having" are intended to be open-ended and mean that there may be additional elements other than the listed elements. It will be recognized by the person of ordinary skill in the art, given the benefit of this disclosure, that various components of the examples can be interchanged or substituted with various components in other examples.

Although certain aspects, examples and embodiments have been described above, it will be recognized by the person of ordinary skill in the art, given the benefit of this disclosure, that additions, substitutions, modifications, and alterations of the disclosed illustrative aspects, examples and embodiments are possible.

What is claimed is:

1. A sorbent device comprising a body comprising a sampling inlet, a base and an open longitudinal diffusion path between the sampling inlet and the base, the sorbent device further comprising a serial arrangement of at least two different sorbent materials each fluidically coupled to the longitudinal diffusion path, in which the sorbent materials are arranged from a material with a weakest sorbent strength to a material with a strongest sorbent strength with the weakest sorbent strength material adjacent to the sampling inlet, in which the sorbent device is effective to sample passively an air space comprising volatile species, in which the open longitudinal diffusion path comprises open space along a longitudinal direction between the sampling inlet and the base and along the serially arranged sorbent materials.

2. The device of claim 1, further comprising a fluid permeable barrier between the at least two different sorbent materials.

3. The device of claim 1, further comprising at least four different sorbent materials, in which the sorbent materials are arranged from a material with a weakest sorbent strength to a material with a strongest sorbent strength with the weakest sorbent strength material adjacent to the sampling inlet.

4. The device of claim 1, further comprising at least six different sorbent materials, in which the sorbent materials are arranged from a material with a weakest sorbent strength to a material with a strongest sorbent strength with the weakest sorbent strength material adjacent to the sampling inlet.

5. The device of claim 1, in which the sorbent device comprises an air gap between the sampling inlet and the weakest strength sorbent material.

6. The device of claim 1, further comprising a carrier in the longitudinal diffusion path of the sorbent device.

7. The device of claim 6, in which the at least two different sorbent materials are disposed in the carrier.

8. The device of claim 6, in which the at least two different sorbent materials are disposed between the carrier and an inner surface of the sorbent device.

9. The device of claim 1, further comprising a void space between the at least two different sorbent materials.

10. The device of claim 1, in which the open longitudinal diffusion path has a variable cross-sectional diameter.

11. The device of claim 1, in which the longitudinal diffusion path comprises a continuous open longitudinal path that spans the full length of the longitudinal diffusion path from the sampling inlet to the base.

12. The device of claim 1, in which the base is configured to couple to an additional sorbent device comprising an open longitudinal diffusion path.

13. The device of claim 12, in which at least one of the base and the sampling inlet comprises a coupling configured to couple to the additional sorbent device, in which coupling of the sorbent device to the additional sorbent device provides fluidic coupling between the longitudinal diffusion path of the sorbent device and the longitudinal diffusion path of the additional sorbent device.

14. The device of claim 1, further comprising a cover coupled to the base, the cover configured to prevent entry of sample into the sorbent device through the base.

15. A kit comprising a sorbent device comprising a body comprising a sampling inlet, a base and an open longitudinal diffusion path between the sampling inlet and the base, the sorbent device further comprising a serial arrangement of at least two different sorbent materials each fluidically coupled to the longitudinal diffusion path, in which the sorbent materials are arranged from a material with a weakest sorbent strength to a material with a strongest sorbent strength with the weakest sorbent strength material adjacent to the sampling inlet, in which the sorbent device is effective to sample passively an air space comprising volatile species and comprises open space from the open longitudinal diffusion path in a longitudinal direction of the serially arranged sorbent materials, in which the kit further comprises instructions for using the sorbent device.

16. The kit of claim 15, further comprising an additional sorbent device configured to passively sample air in an environment, the additional sorbent device comprising a body comprising a sampling inlet, a base and a longitudinal diffusion path between the sampling inlet and the base, the additional sorbent device further comprising at least one sorbent material fluidically coupled to the longitudinal diffusion path of the additional sorbent device, in which the sorbent material of the additional sorbent device is different from the sorbent materials of the sorbent device.

17. The kit of claim 16, in which the additional sorbent device further comprises a coupling configured to couple to the sorbent device to provide fluidic coupling between the longitudinal diffusion path of the sorbent device and the longitudinal diffusion path of the additional sorbent device.

18. The kit of claim 15, further comprising at least one standard.

19. The kit of claim 15, further comprising a plurality of additional sorbent devices each comprising a body comprising a sampling inlet, a base, a longitudinal diffusion path between the sampling inlet and the base, in which the plurality of additional sorbent devices each comprise a different sorbent medium than present in the sorbent device, and in which the plurality of additional sorbent devices each comprise a coupling to provide fluidic coupling between the longitudinal diffusion paths.

20. The kit of claim 15, further comprising a thermal desorption analyzer for use with the sorbent device.

* * * * *